(12) United States Patent
Hantash et al.

(10) Patent No.: US 9,567,368 B2
(45) Date of Patent: Feb. 14, 2017

(54) PEPTIDE TYROSINASE ACTIVATORS

(71) Applicant: Escape Therapeutics, Inc., San Jose, CA (US)

(72) Inventors: Basil M. Hantash, East Palo Alto, CA (US); Anan Abu Ubeid, San Jose, CA (US)

(73) Assignee: Escape Therapeutics, Inc., San Jose, CA (US)

( * ) Notice: Subject to any disclaimer, the term of this patent is extended or adjusted under 35 U.S.C. 154(b) by 0 days.

(21) Appl. No.: 14/555,316

(22) Filed: Nov. 26, 2014

(65) Prior Publication Data
US 2015/0152139 A1  Jun. 4, 2015

Related U.S. Application Data

(60) Provisional application No. 61/910,268, filed on Nov. 29, 2013.

(51) Int. Cl.
*A61K 38/00* (2006.01)
*A61P 17/00* (2006.01)
*C07K 7/06* (2006.01)
*A61K 8/64* (2006.01)
*A61Q 19/04* (2006.01)

(52) U.S. Cl.
CPC . *C07K 7/06* (2013.01); *A61K 8/64* (2013.01); *A61Q 19/04* (2013.01); *A61K 2800/78* (2013.01)

(58) Field of Classification Search
None
See application file for complete search history.

(56) References Cited

U.S. PATENT DOCUMENTS

| 5,492,894 | A |  | 2/1996 | Bascom et al. |
| 5,962,417 | A |  | 10/1999 | Gilchrest et al. |
| 7,902,329 | B2 | * | 3/2011 | Hantash .................. A61K 8/64 530/326 |
| 9,320,698 | B2 | * | 4/2016 | Hantash .................. C07K 7/06 |

FOREIGN PATENT DOCUMENTS

| WO | WO2007/032029 | * | 9/2006 | ............. A61K 38/04 |
| WO | 2009/034188 A1 |  | 3/2009 | |
| WO | 2013/138681 A1 |  | 9/2013 | |

OTHER PUBLICATIONS

Betts et al. Amino Acid Properties and Consequences of Substitutions. Bioinformatics for Geneticists. Chapter 14. 2003. pp. 289-316.*
International Search Report, PCT/US14/067783, Mar. 11, 2015, 3 pages.

* cited by examiner

*Primary Examiner* — Marcela M Cordero Garcia
(74) *Attorney, Agent, or Firm* — Aka Chan LLP

(57) ABSTRACT

Peptides that increase melanin synthesis are provided. These peptides include pentapeptides YSSWY (SEQ ID NO: 1), YRSRK (SEQ ID NO: 2), and their variants. The peptides may activate the enzymatic activity of tyrosinase to increase melanin synthesis. The pharmaceutical, cosmetic, and other compositions including the peptides are also provided. The methods of increasing melanin production in epidermis of a subject are provided where the methods include administering compositions comprising an amount of one or more peptides effective to increase the melanin production. The methods also include treating vitiligo or other hypopigmentation disorders with compositions including one or more peptides.

17 Claims, 6 Drawing Sheets

P9

P10

SEQUENCE LISTING

```
<160> NUMBER OF SEQ ID NOS: 10

<210> SEQ ID NO 1
<211> LENGTH: 5
<212> TYPE: PRT
<213> ORGANISM: artificial
<220> FEATURE:
<223> OTHER INFORMATION: synthetic peptide

<400> SEQUENCE: 1

Tyr Ser Ser Trp Tyr
1               5

<210> SEQ ID NO 2
<211> LENGTH: 5
<212> TYPE: PRT
<213> ORGANISM: artificial
<220> FEATURE:
<223> OTHER INFORMATION: synthetic peptide

<400> SEQUENCE: 2

Tyr Arg Ser Arg Lys
1               5

<210> SEQ ID NO 3
<211> LENGTH: 4
<212> TYPE: PRT
<213> ORGANISM: artificial
<220> FEATURE:
<223> OTHER INFORMATION: synthetic peptide

<400> SEQUENCE: 3
```

Tyr Ser Ser Trp
1

<210> SEQ ID NO 4
<211> LENGTH: 4
<212> TYPE: PRT
<213> ORGANISM: artificial
<220> FEATURE:
<223> OTHER INFORMATION: synthetic peptide

<400> SEQUENCE: 4

Ser Ser Trp Tyr
1

<210> SEQ ID NO 5
<211> LENGTH: 4
<212> TYPE: PRT
<213> ORGANISM: artificial
<220> FEATURE:
<223> OTHER INFORMATION: synthetic peptide

<400> SEQUENCE: 5

Tyr Arg Ser Arg
1

<210> SEQ ID NO 6
<211> LENGTH: 4
<212> TYPE: PRT
<213> ORGANISM: artificial
<220> FEATURE:
<223> OTHER INFORMATION: synthetic peptide

<400> SEQUENCE: 6

Arg Ser Arg Lys
1

<210> SEQ ID NO 7
<211> LENGTH: 5
<212> TYPE: PRT
<213> ORGANISM: artificial
<220> FEATURE:
<223> OTHER INFORMATION: synthetic peptide

<400> SEQUENCE: 7

Tyr Thr Thr Trp Tyr
1               5

<210> SEQ ID NO 8
<211> LENGTH: 5
<212> TYPE: PRT
<213> ORGANISM: artificial
<220> FEATURE:
<223> OTHER INFORMATION: synthetic peptide

<400> SEQUENCE: 8

Tyr Arg Thr Arg Lys
1               5

<210> SEQ ID NO 9
<211> LENGTH: 5
<212> TYPE: PRT
<213> ORGANISM: artificial
<220> FEATURE:
<223> OTHER INFORMATION: synthetic peptide

<400> SEQUENCE: 9

```
Tyr Ser Ser Tyr Tyr
1               5

<210> SEQ ID NO 10
<211> LENGTH: 5
<212> TYPE: PRT
<213> ORGANISM: artificial
<220> FEATURE:
<223> OTHER INFORMATION: synthetic peptide

<400> SEQUENCE: 10

Tyr Lys Ser Arg Lys
1               5
```

PEPTIDE TYROSINASE ACTIVATORS

CROSS-REFERENCE TO RELATED APPLICATIONS

This application claims the benefit of U.S. patent application 61/910,268, filed Nov. 29, 2013, entitled "Pentapeptide Tyrosinase Activators," which is incorporated by reference along with all other references cited in this application.

SEQUENCE LISTING

This application incorporates by reference a sequence listing entitled "P9P10sequence_ST25.txt" (2 kilobytes) which was created Nov. 25, 2014 and filed electronically with this application.

BACKGROUND OF THE INVENTION

The present invention relates to the field of novel biological agents, and specifically pentapeptides and other peptides that can increase pigment production by activating tyrosinase.

One of the main risk factors for skin carcinogenesis is exposure to ultraviolet radiation (UVR), whether from sun or tanning beds. The incidence of skin cancer has increased dramatically in recent decades, and now accounts for every third new cancer case diagnosed in developed countries. A meta-analysis conducted by the International Agency for Research on Cancer (IARC) showed use of tanning beds before age 30 increased melanoma risk by 75 percent relative to naïve individuals (IARC-2007), and increased risk of basal cell carcinoma (BCC) and squamous cell carcinoma (SCC). Consequently, the IARC has classified tanning beds as carcinogenic to humans.

Despite this, tanning bed use among young women remains high. Each day, more than 1 million people tan in one of 50,000 facilities in the United States, 70 percent of which are females 16 to 49 years of age. The desire for tan skin underlies this increase, as some surveys have shown tan skin corresponds with a perception of healthier skin and well being.

Two main defense mechanisms to help protect against UVR exist—epidermal thickening and the stimulation of melanin synthesis. However, melanin content levels are based on an individual's melanogenic potential. Hence, fair skinned individuals can be at higher risk. The inverse correlation between skin pigmentation and the incidence of sun-induced skin cancers supports the photoprotective role of melanin. In the United States, the rates of BCC and SCC and melanoma are 50 and 10 times higher, respectively, in Caucasians than in African Americans. Moreover, in black and white skin after irradiation with UVR, a five-fold less radiation reaches the upper dermis of black skin compared to white skin. This result can be attributed to factors including increased melanin content, its more efficient distribution, and increased stratum corneum thickness.

Therefore, there is a need to developing a UV-less method of enhancing melanogenesis. Specifically, there is a need to develop biological compounds and methods to enhance melanin production, without the DNA damage associated with tanning beds and solar UVR.

BRIEF SUMMARY OF THE INVENTION

Melanin is the primary substance that provides pigment (color) to skin, hair, and eyes in humans. Melanin pigmentation is largely responsible for normal skin, hair, and eye color, and provides protection against ultraviolet light damage from sunlight and other light sources. Some individuals are unable to produce normal amounts of melanin and as a result, can have uneven or no pigmentation in the skin, hair, and eyes. Some conditions include vitiligo (i.e., depigmentation of parts of the skin), piebaldism, albinism (complete or partial absence of pigment in the skin, hair and eyes), amelanism, hypochromia, and other hypopigmentation disorders. Patients with these disorders can experience partial to depigmentation of skin, hair, and eye color.

The present invention relates to the development of a UV-less method of enhancing melanogenesis (i.e., the production of melanin) by targeting tyrosinase, a key enzyme in the production of melanin. Specifically, two novel pentapeptides, P9, P10, and their variant forms, may allosterically activate tyrosinase to enhance melanin production, without the DNA damage associated with tanning beds and solar UVR.

With the present invention, these peptides can increase melanin synthesis, thereby increasing the pigmentation of the skin, hair, and eyes. One or more of these peptides can be administered to patients with pigmentation disorders (including vitiligo, piebaldism, albinism, and other hypopigmentation disorders) to increase pigment production via activation of the tyrosinase enzyme. One or more peptides can be administered to patients to reduce symptoms of photosensitivity disorders such as erythropoietic protoporphyria (EPP), solar urticarial (SU) and polymorphic light eruption (PLE).

In the present invention, a peptide increases melanin production by activation of tyrosinase as shown and described in this application.

In implementations, certain peptide sequences according to the present invention are exemplified as:

YSSWY (SEQ ID NO: 1), also referred as "P9" peptide; and

YRSRK (SEQ ID NO: 2), also referred as "P10" peptide.

One or more peptides can be selected from the group comprising YSSWY (SEQ ID NO: 1) or YRSRK (SEQ ID NO: 2), or a variant (e.g., a fragment, a peptide with conservative amino acid substitution) of these, or a combination of these for use in compositions and treatments.

In a specific implementation, the peptide has an amino acid sequence essentially identical to one of YSSWY (SEQ ID NO: 1) or YRSRK (SEQ ID NO: 2).

In a specific implementation, the peptide has between one and three conservative amino acid substitutions in YSSWY (SEQ ID NO: 1) or YRSRK (SEQ ID NO: 2).

In a specific implementation, the peptide has one conservative amino acid substitution in YSSWY (SEQ ID NO: 1) or YRSRK (SEQ ID NO: 2).

In a specific implementation, the peptide is modified by a modifying group, the modifying group being either an acylation or an acetylation of an amino-terminal end, or amidation, lipidation, methylation, or an esterification of a carboxy-terminal end, or both.

In a specific implementation, the peptide is a pentapeptide.

In a specific implementation, the peptide activates tyrosinase activity in patients with vitiligo. In another specific implementation, the peptide activates tyrosinase activity in patients with pigment loss in skin. In another specific implementation, the peptide activates tyrosinase activity and melanin production in patients with melanoma type cancer. In yet another specific implementation, the peptide activates tyrosinase activity and melanin production in patients with nonmelanoma type skin cancer.

In a specific implementation, a cosmetic or pharmaceutical composition is provided where the composition comprises an amount of one or more peptides in accordance with the present invention to increase melanin production. In embodiments of the invention, one or more peptides can be selected from the group comprising YSSWY (SEQ ID NO: 1) or YRSRK (SEQ ID NO: 2), or a variant (e.g., a fragment or a peptide with conservative amino acid substitution) of these, or a combination of these.

In a specific implementation, a formulation including one or more peptides as shown and described in this application activates melanin production in skin for sunless tanning. In a specific implementation, a sunless tanning product (e.g., a cream, lotion, gel, spray, and others) includes the formulation including the one or more peptides.

In the present invention, a method of treating vitiligo and other hypopigmentation disorders includes using one or more peptides according to the present invention that increase pigment production via activation of tyrosinase.

A method of treating a disorder involving pigment loss includes using one or more peptides according to the present invention that increase pigment production via activation of tyrosinase.

A method of increasing melanin to protect against skin cancers of melanoma type includes using one or more peptides according to the present invention that increase pigment production via activation of tyrosinase.

A method of increasing melanin to protect against skin cancers of nonmelanoma type includes using one or more peptides according to the present invention that increase pigment production via activation of tyrosinase.

A method of increasing melanin to reduce symptoms of photosensitivity disorders (e.g., EPP, SU, PLE, and the like) includes using one or more peptides according to the present invention that increase pigment production via activation of tyrosinase.

The present invention is further directed to kits and compositions containing the present peptides, and methods of treatment of conditions involving expression of tyrosinase. The present peptides can be administered topically for the treatment of conditions involving melanin production or tyrosinase activity in the skin. Other formulations are useful in treating tyrosinase activity in other regions of the body and may be administered internally.

Other objects, features, and advantages of the invention will become apparent upon consideration of the following detailed description and the accompanying drawings, in which like reference designations represent like features throughout the figures.

DETAILED DESCRIPTION OF THE INVENTION

Figures 1A, 1B:
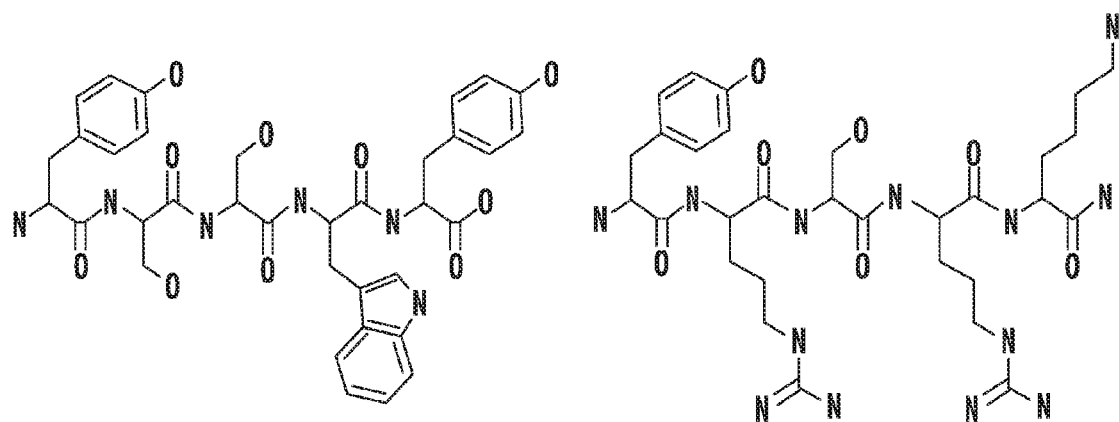
FIG. 1A shows an oligopeptide amino acid sequence and structure for a pentapeptide P9.
FIG. 1B shows an oligopeptide amino acid sequence and structure for a pentapeptide P10.

Skin cancer is the most common malignancy among Caucasians in the United States, and its incidence has been rising rapidly especially in young women in large part due to their use of tanning beds. For these individuals, the perceived benefits of indoor tanning appeared to outweigh the well-known risks of premature skin aging, skin cancer, and immunosuppression.

The head and neck accounts for about 80 percent to about 90 percent of new BCC and SCC cases, although trunk involvement can be found in younger patients. Tanning bed use may underlie these recent shifts.

The risk of skin cancer is higher in individuals with lower melanin content. Racial differences in skin color may primarily be due to differences in tyrosinase activity. Melanocytes derived from African skin demonstrate up to 10 times more activity and melanin production than melanocytes from Caucasian skin. However, this is not due to a greater abundance of tyrosinase, as both skin types contain a similar density of tyrosinase molecules.

Stimulating melanin production without UVR exposure offers one potential photoprotective modality in addition to daily sun protection factor (SPF) 50 sunscreen application. Since use of sunscreen in of itself has not been an adequate strategy, in embodiments of the present invention, agents that stimulate melanogenesis in the absence of UVR have been developed and provided.

Effective prevention strategies for skin cancer are urgently needed to reduce its increasing incidence and health burden. With their ability to induce prolonged melanin production devoid of UVR exposure, peptides according to embodiments of the present invention can offer a clinically relevant approach for safely increasing melanin production. Enhancing epidermal pigmentation may help fight the alarming spike in tanning bed use while replacing non-photoprotective sunless tanning products with a photoprotective alternative. Other future clinical uses include prophylactic treatment of photosensitivity skin disorders.

The peptides in accordance with the present invention may also be used as research and development tools in basic science investigation, in diagnostic applications, as therapeutics for the treatment of vitiligo, albinisum, piebaldism, and other hypopigmentation disorders and for the protection against skin cancers of melanoma and nonmelanoma type, and the like, by increasing melanin production. In addition, the peptides in accordance with the present invention may also be employed in methods for pigmenting (coloring) skin grafts (autografts or allografts) in vitro and in vivo. They can also be used as a sun-light independent human skin tanning agent.

Peptides

In one aspect of the present invention, peptides that increase melanin production are provided. Not wishing to be bound by any one theory, the present peptides may enhance melanin synthesis in cells by activating tyrosinase enzyme activity as shown in the example section below.

As used in this application, the term "melanin" can refer to a group of natural pigments found in most organisms. Melanin is produced by the oxidation of the amino acid tyrosine, followed by polymerization. Three basic types of melanin include eumelanin, pheomelanin, and neuromelanin. The most common type is eumelanin and is produced in "black" and "brown" subtypes. The present peptides may increase synthesis of one or more types of melanin.

The term, "increasing" or "enhancing" melanin production by a peptide, can refer to the melanin content or production becoming greater in amount or degree by at least 10, 20, 30, 40, 50, 60, 70, 80, 90, or 100 percent or by at least 1.5-fold, 2.0-fold or more, when a peptide in accordance with the present invention is added to cells, skin, or body (in vivo, ex vivo, or in vitro) compared to untreated control (e.g., treated medium only) under substantially similar conditions. In testing the effects of peptides on melanin production, any suitable melanin production assays may be employed including assays described in this application.

The term "tyrosinase" can refer to monophenol monooxygenase (EC 1.14.18.1; CAS number: 9002-10-2), an enzyme that catalyzes the oxidation of phenols (such as tyrosine). It is a copper-containing enzyme present in plant and animal tissues that catalyzes the production of melanin and other pigments from tyrosine by oxidation. All tyrosinases have in common a binuclear type-3 copper center within their active site. Here two copper atoms are each coordinated with three histidine residues. Matoba et al., "Crystallographic evidence that the dinuclear copper center of tyrosinase is flexible during catalysis," *J Biol Chem.*, 2006 Mar. 31; 281(13): 8981-90. Epub 2006 Jan. 25, disclose a three-dimensional model of a tyrosinase catalytic center.

The term, "activating" tyrosinase can refer to increasing tyrosinase activity with an agent such as peptides in accordance with the present invention. The term "increasing" tyrosinase activity by a peptide, can refer to tyrosine activity becoming greater in amount or degree by at least 10, 20, 30, 40, 50, 60, 70, 80, 90, or 100 percent, or by at least 1.5-fold, 2-fold, or more when a peptide in accordance with the present invention is added to cells, skin, or body (in vivo, ex vivo, or in vitro) compared to untreated control under substantially similar conditions. In testing the effects of peptides on tyrosinase activity, any suitable tyrosinase assays known in the art or described in this application may be employed.

The term "peptide" can refer to a sequence of two or more amino acids linked together by peptide bonds or by modified peptide bonds. When the amino acids are α-amino acids, either the L-optical isomer or the D-optical isomer may be used. Additionally, unnatural amino acids, for example, β-alanine, phenylglycine and homoarginine are also meant to be included. In embodiments of the present invention, peptides are two or more amino acid monomers long and may include up to 20 amino acid monomers. Standard abbreviations for amino acids are used as described below.

The present peptides include peptide analogues or peptide derivatives or peptidomimetics that retain the ability to increase the production of melanin by activating a tyrosinase activity within a cell. For example, the peptides in accordance with the present invention may be modified to increase its stability, bioavailability, solubility, and the like. The terms "peptide analogue," "peptide derivative," and "peptidomimetic" are used in this application to include molecules that mimic the chemical structure of a peptide and retain the functional properties of the peptide. Approaches to designing peptide analogs are known in the art. For example, see Farmer, P. S. in Drug Design (E. J. Ariens, ed.) Academic Press, New York, 1980, vol. 10, pp. 119-143; Ball. J. B. and Alewood, P. F. (1990) *J. Mol. Recognition* 3:55; Morgan, B. A. and Gainor, J. A. (1989) *Ann. Rep. Med. Chem.* 24:243; and Freidinger, R. M. (1989) *Trends Pharmacol. Sci.* 10:270. Examples of peptide analogues, derivatives and peptidomimetics include peptides substituted with one or more benzodiazepine molecules (see e.g., James, G. L. et al. (1993) *Science* 260:1937-1942), peptides with methylated amide linkages and "retro-inverso" peptides (see U.S. Pat. No. 4,522,752 by Sisto). Peptide analogues, peptide derivatives and peptidomimetic are described in further detail below.

Peptides of the present invention may comprise residues from any of the naturally occurring amino acids, or from nonnaturally occurring amino acids. These naturally occurring and nonnaturally-occurring amino acids may be in the D or L configuration, or may include both dextrorotary forms. The terms D and L are used in this application as they are known to be used in the art. Peptides of the invention include single amino acids and short spans (e.g., 1-20) of amino acids. In addition, modified peptides of the present invention may also include a monomer or dimer.

The standard single letter and three letter codes for amino acids are used in this application and are in table A below.

TABLE A

| A (Ala) Alanine | C (Cys) Cysteine | D (Asp) Aspartic acid |
|---|---|---|
| E (Glu) Glutamic acid | F (Phe) Phenylalanine | G (Gly) Glycine |
| H (His) Histidine | I (Ile) Isoleucine | K (Lys) Lysine |
| L (Leu) Leucine | M (Met) Methionine | N (Asn) Asparagine |
| P (Pro) Proline | Q (Gln) Glutamine | R (Arg) Arginine |
| S (Ser) Serine | T (Thr) Threonine | V (Val) Valine |
| W (Trp) Tryptophan | Y (Tyr) Tyrosine | |

As described above, the indicated residues may be the naturally occurring L amino acid, or a modification of these, that is, a chemical modification, an optical isomer, or a link to a modifying group. It is contemplated that specific modifications may be made within the peptide that maintain the ability of the present peptides to specifically increase the melanin production by increasing the activity of tyrosinase whereby it catalyzes the first two steps in the pathway for pigment synthesis: hydroxylation of the amino acid tyrosine into dihydroxyphenylalanine (DOPA) or the subsequent oxidation into dopaquinone, or a combination of these.

In one implementation, specific modifications may be made in a particular sequence in order to confer some additional desirable property to the peptide. Certain amino acids may be substituted for other amino acids in a protein structure without appreciable loss of peptide activity. Since it is the interactive capacity and nature of a peptide that defines that peptide's biological functional activity, certain amino acid sequence substitutions can be made even in a short peptide sequence and nevertheless obtain a peptide with like properties. Thus, in embodiments of the present invention, various changes may be made in the sequence of the peptides in accordance with the present invention without appreciable loss of biological utility or activity and perhaps may enhance desired activities.

For example, in designing peptide constructs with melanin production increase and/or tyrosinase activating properties, substitutions may be used which modulate one or more properties of the molecule. Such variants typically contain the exchange of one amino acid for another at one or more sites within the peptide. For example, certain amino acids may be substituted for other amino acids in a peptide structure in order to enhance the interactive binding capacity of the structures. One may also substitute D- for L-amino acids, or include certain side chain covalent modifications.

In making such changes, the hydropathic index of amino acids may be considered.

The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

In modifying the presently exemplified sequences, certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those that are within ±1 are particularly preferred, and those within ±0.5 are even more particularly preferred.

Substitution of like amino acids can also be made effectively on the basis of hydrophilicity. U.S. Pat. No. 4,554,101, which is incorporated by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In modifying the exemplified sequences, amino acid substitutions may also be generally based on the relative similarity of the amino acid side-chain substituents, for example, their hydrophobicity, hydrophilicity, charge, size, and the like but may nevertheless be made to highlight a particular property of the peptide. Exemplary substitutions that take various of the foregoing characteristics into consideration are well known to those of skill in the art and include: arginine and lysine, which, with histidine, are basic at physiological pH; glutamate and aspartate (which are acidic); serine and threonine; glutamine and asparagine; and valine, leucine and isoleucine.

The naturally occurring amino acid side chains are illustrated in tables B and C, in which * represents the attachment point to the compound's backbone.

TABLE B

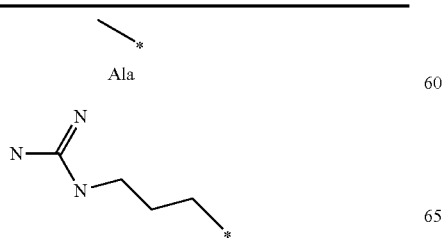

Ala

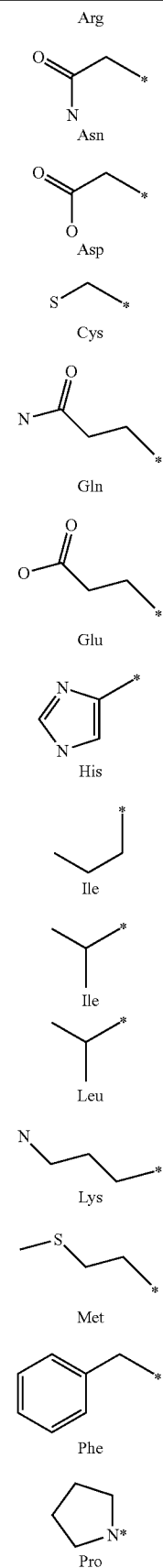

Arg

Asn

Asp

Cys

Gln

Glu

His

Ile

Ile

Leu

Lys

Met

Phe

Pro

TABLE B-continued

Ser

Thr

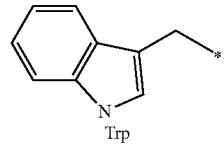
Trp

Val

TABLE C

Ala

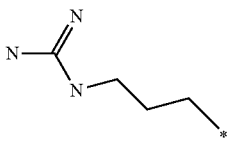
Arg

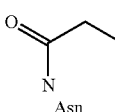
Asn

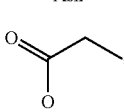
Asp

Cys

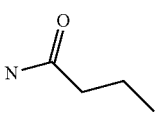
Gln

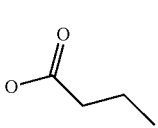
Glu

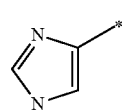
His

TABLE C-continued

Ile

Ile

Leu

Lys

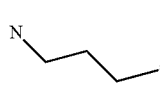
Met

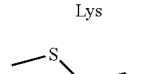
Phe

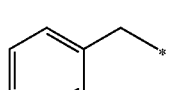
Pro

Ser

Thr

Trp

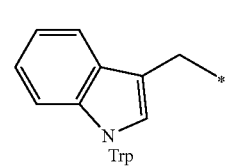
Val

The amino acids of the peptides of the present invention may also be modified so that amino groups may be acylated, alkylated or arylated. Benzyl groups may be halogenated, nitrosylated, alkylated, sulfonated or acylated.

Various chemically modified amino acids may be incorporated into the present peptides. Examples of these include:
Acetylated
N-acetyl-L-alanine, N-acetyl-L-arginine; N-acetyl-L-asparagine; N-acetyl-L-aspartic acid; N-acetyl-L-cysteine; N-acetyl-L-glutamine; N-acetyl-L-glutamic acid; N-acetyl-glycine; N-acetyl-L-histidine; N-acetyl-L-isoleucine;

N-acetyl-L-leucine; N2-acetyl-L-lysine; N6-acetyl-L-lysine; N-acetyl-L-methionine; N-acetyl-L-phenylalanine; N-acetyl-L-proline; N-acetyl-L-serine; N-acetyl-L-threonine; N-acetyl-L-tryptophan; N-acetyl-L-tyrosine; N-acetyl-L-valine.

Amidated

L-alanine amide, L-arginine amide

Formylated

N-formyl-L-methionine

Hydroxylated 4-hydroxy-L-proline

Lipid Modified

S-farnesyl-L-cysteine, S-geranylgeranyl-L-cysteine, N-palmitoyl-L-cysteine, S-palmitoyl-L-cysteine, N-myristoyl-glycine, N6-myristoyl-L-lysine Methylated N-methyl-L-alanine, N,N,N-trimethyl-L-alanine, omega-N,omega-N-dimethyl-L-arginine L-beta-methylthioaspartic acid, N5-methyl-L-glutamine, L-glutamic acid 5-methyl ester 3'-methyl-L-histidine, N6-methyl-L-lysine, N6,N6-dimethyl-L-lysine, N6,N6,N6-trimethyl-L-lysine, N-methyl-L-methionine, N-methyl-L-phenylalanine Phosphorylated omega-N-phospho-L-arginine, L-aspartic 4-phosphoric anhydride, S-phospho-L-cysteine, l'-phospho-L-histidine, 3'-phospho-L-histidine, O-phospho-L-serine, O-phospho-L-threonine, 04'-phospho-L-tyrosine Other L-selenocysteine, L-selenomethionine, L-3-oxoalanine, 2-pyrrolidone-5-carboxylic acid, L-glutamyl 5-glyceryl-phosphorylethanolamine, 2'-[3-carboxamido-3-(trimethylammonio)propyl]-L-histidine (diphthamide), N6-biotinyl-L-lysine, N6-(4-amino-2-hydroxybutyl)-L-lysine (hypusine), N6-retinal-L-lysine Other modifications to the amino acids contained in the present peptides are known in the art, and described, for example in Kuhner et al. U.S. Pat. No. 6,858,581, which describes chemically modified antimicrobial peptides.

Modulating Groups

In a peptide modulator of the invention having the formula shown above, a modulating group for improved cellular uptake or efficacy or formulation may be attached directly or indirectly to the peptide in accordance with the present invention. For example, the modulating group can be directly attached by covalent coupling to the peptide or the modulating group can be attached indirectly by a stable non-covalent association. In one embodiment of the invention, the modulating group is attached to the amino-terminus of the peptide of the modulator. Alternatively, in another embodiment of the invention, the modulating group is attached to the carboxy-terminus of the peptide of the modulator.

In yet another embodiment, the modulating group is attached to the side chain of at least one amino acid residue of the peptide of the compound (e.g., through the epsilon amino group of a lysyl residue(s), through the carboxyl group of an aspartic acid residue(s) or a glutamic acid residue(s), through a hydroxy group of a tyrosyl residue(s), a serine residue(s) or a threonine residue(s) or other suitable reactive group on an amino acid side chain). Further guidance on preparing such modulating groups is found in U.S. Pat. No. 5,854,204.

Another modulating group for enhancing cell permeability is an amino acid sequence, which is recognized and taken up by melanocytes. D'Ursi et al., "A Membrane-Permeable Peptide Containing the Last 21 Residues of the GS Carboxyl Terminus Inhibits GS-Coupled Receptor Signaling in Intact Cells: Correlations between Peptide Structure and Biological Activity," Mol Pharmacol 69:727-736, 2006 disclose cell-penetrating peptides which are able to transport covalently attached cargoes such as peptide or polypeptide fragments of endogenous proteins across cell membranes. The authors coupled their peptide to the 16-residue fragment penetrating, and such fragment may be coupled to the peptides disclosed in this application.

Thus, the term modulating group can refer to a small organic molecule linked to the peptide to affect its activity, either by improving its stability uptake or the like, or by providing additional increase in melanin production or tyrosinase activation, or a combination of these.

In an embodiment, the modifying group(s) comprises a cyclic, heterocyclic or polycyclic group. The term "cyclic group," as used in this application, is intended to include cyclic saturated or unsaturated (i.e., aromatic) group having from about 3 to 10, or about 4 to 8, or about 5 to 7, carbon atoms. Exemplary cyclic groups include cyclopropyl, cyclobutyl, cyclopentyl, cyclohexyl, and cyclooctyl. Cyclic groups may be unsubstituted or substituted at one or more ring positions. Thus, a cyclic group may be substituted with, e.g., halogens, alkyls, cycloalkyls, alkenyls, alkynyls, aryls, heterocycles, hydroxyls, aminos, nitros, thiols amines, imines, amides, phosphonates, phosphines, carbonyls, carboxyls, silyls, ethers, thioethers, sulfonyls, sulfonates, selenoethers, ketones, aldehydes, esters, —$CF_3$, —CN, or the like.

In another embodiment, the modulating group comprises a fatty acid bonded to the peptide, in order to increase uptake through the skin. Suitable fatty acids (which are meant to include the corresponding ester) include fatty acid ester emollient selected from the group consisting of methyl palmitate, methyl stearate, isopropyl laurate, isopropyl myristate, isopropyl palmitate, ethylhexyl palmitate, lauryl lactate and cetyl lactate.

The term "heterocyclic group" is intended to include cyclic saturated or unsaturated (i.e., aromatic) group having from about 3 to 10, or about 4 to 8, or about 5 to 7, carbon atoms, where the ring structure includes about one to four heteroatoms. Heterocyclic groups include pyrrolidine, oxolane, thiolane, imidazole, oxazole, piperidine, piperazine, morpholine. The heterocyclic ring can be substituted at one or more positions with such substituents as, for example, halogens, alkyls, cycloalkyls, alkenyls, alkynyls, aryls, other heterocycles, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, —$CF_3$, —CN, or the like. Heterocycles may also be bridged or fused to other cyclic groups.

The term "pentapeptide" can refer to a sequence of five amino acids linked together by peptide bonds or by modified peptide bonds. The term "oligopeptide," often called peptide, can consist of two to twenty amino acids.

In specific embodiments, pentapeptides that increase melanin production and tyrosinase activity are provided. The pentapeptides may have one of the following sequences:

```
                                                   (SEQ ID NO: 1)
YSSWY;
or (SEQ ID NO: 2)
YRSRK.
```

In embodiments of the present invention, SEQ ID NO: 1 is also referred to as pentapeptide P9, and SEQ ID NO: 2 is also referred to as pentapeptide P10. One or more of these pentapeptides, alone or in combination, enhance melanogenesis and increase tyrosinase activity.

In some implementations, variant forms of pentapeptides P9 and P10 may be used to increase melanin production and tyrosinase activity in cells. The term "variant" refers to a peptide that differs, for example, from the sequence of pentapeptides P9 or p10 while still retaining P9's or P10's essential properties, respectively. A variant form retains the ability to increase melanin production and tyrosinase activity in cells, allosteric activation of tyrosinase, or any combination of these. For example, the melanin production induced by P9 or P10 variant is at least about 50, 60, 70, 80, 90, or 100 percent of melanin production induced by P9 or P10, respectively. Similarly, tyrosinase activity induced by P9 or P10 variant is at least about 50, 60, 70, 80, 90, or 100 percent of tyrosinase activity induced by P9 or P10, respectively. Generally, the sequences of the reference peptide and those of the variant are quite similar and, in some regions, identical. In some implementations, the use of pentapeptides P9 or P10 described in the present invention also includes the use of their variants.

In an embodiment, a variant may be a fragment of pentapeptides P9 or P10 that has four or less amino acids. Examples of these fragments include:

```
                                          (SEQ ID NO: 3)
YSSW;

(SEQ ID NO: 4)
SSWY;

(SEQ ID NO: 5)
YRSR;
and (SEQ ID NO: 6)
RSRK.
```

In some embodiments, variants of pentapeptides P9 and P10 may include a peptide with more than five amino acids. In some embodiments, a variant peptide may have up to about 20 amino acids long. In certain embodiments, a variant peptide may include additional amino acids on either amino-terminal or carboxy-terminal side, or both sides of pentapeptide P9. In other embodiments, a variant peptide may include additional amino acids on either amino-terminal or carboxy-terminal side, or both sides of pentapeptide P10. Any suitable number of amino acids can be added on either terminal sides of P9 or P10.

In some embodiments, variants of P9 and P10 may include homologous sequences of P9 and P10 that have an amino acid sequence essentially identical to P9 and P10 sequences, respectively. As used in this application, the term "sequence identity" refers to amino acid residues in the two sequences, which are the same when aligned for maximum correspondence. Optimal alignment of sequences for comparison can be conducted, e.g., by the local homology algorithm of Smith and Waterman, *Adv. Appl. Math*, 2: 482 (1981), by the homology alignment algorithm of Needleman and Wunsch, *J. Mol. Biol.* 48:443 (1970), by the search for similarity method of Pearson and Lipman, *Proc. Natl. Acad. Sci.* (*U.S.A.*) 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection. Sequence identity may be calculated on the basis of residues identical to a reference sequence. For example, for YSSWY (SEQ ID NO: 1), having 5 residues, one may have 3 identical residues and have ⅗ or 60 percent sequence identity. Because of the limited length of the peptides, at least 60 percent identity is considered "essentially identical" when changes are made according to the present teachings. One may also have ⅘ (80 percent) sequence identity. For example, a residue may be eliminated, such as serine, and replaced with threonine, which results in the new sequence having 80 percent sequence identity.

The terms "substantial identity" as used in this application denotes a characteristic of a peptide sequence, where the peptide comprises a sequence that has at least 60 percent sequence identity, optionally at least 80 percent identity and in some embodiments 90 to 95 percent sequence identity as compared to a reference sequence over a comparison window of the entire peptide length. Substantial identity can further involve a conservative substitution of an amino acid. The term "essentially identical" in the context of the present five residue peptides means that two amino acid substitutions are permitted, according to the present teachings specifically providing guidance in making substitutions, and the definition above. For longer sequences, more amino acid substitutions may be permitted.

In specific embodiments, variants of P9 and P10 may include peptides with a conservative substitution of one or more amino acid residues in P9 or P10 with similar characteristics. Conservative amino acid substitutions are those that take place within the family of amino acids that are related in their side chains as discussed above. Examples of conservative substitution include substitution between aromatic amino acids such as a substitution among phenylalanine, tryptophan, and tyrosine; substitution between hydrophobic amino acids such as a substitution among leucine, isoleucine, and valine; substitution between polar amino acids such as a substitution between glutamine and asparagine; substitution between basic amino acids such as a substitution among lysine, arginine, and histidine; substitution between acidic amino acids such as a substitution between aspartic acid and glutamic acid; substitution between amino acids having a hydroxyl group such as a substitution between serine and threonine. For example, it is reasonable to expect that an isolated replacement of a threonine with a serine or replacement of an arginine with a lysine will not have a major effect on the binding or properties of the resulting variant peptide.

In certain embodiments, in variants of P9 and P10, tyrosine of P9 or P10 can be replaced with either phenylalanine or tryptophan; serine of P9 or P10 can be replaced with threonine; tryptophan of P9 can be replaced with phenylalanine or tyrosine; arginine of P10 can be replaced with lysine or histidine; lysine of P10 can be replaced with arginine or histidine.

In some embodiments, variants of pentapeptides P9 and P10 have between one to three conservative substitutions. In a specific embodiment, variants of pentapeptides P9 and P10 may have two conservative substitutions. In specific embodiments, variants of pentapeptides P9 and P10 may have one conservative substitution. Examples of variants of pentapeptides P9 and P10 with one conservative substitution may include:

```
                                          (SEQ ID NO: 7)
YTTWY;

(SEQ ID NO: 8)
YRTRK;
```

-continued

YSSYY; (SEQ ID NO: 9)

YKSRK; (SEQ ID NO: 10)

and the like.

The peptides in accordance with the present invention can be chemically synthesized using standard chemical peptide synthesis techniques (solid phase or liquid phase). The chemical synthesis of peptides are well known to those of skill in the art and are described, for example, by Barany and Merrifield (1963) Solid-Phase Peptide Synthesis; pages 3-284 in The Peptides: Analysis, Synthesis, Biology, Vol. 2: Special Methods in Peptide Synthesis, Part A. Automatic peptide synthesizers are well-known in the art, and peptides can also be custom ordered through third party vendors such as Bio Basic, Inc. (Ontario, Canada). In other embodiments, peptides can be expressed using host organisms (e.g., bacterial, plant, fungal, and others), isolated, and purified using techniques well-known in the art. The peptides can then be stored in any suitable form—lyophilized form, powder, solution, and the like.

In some embodiments, the peptides in accordance with the present invention may be modified to improve resistance to degradation, cell penetration, increased affinity to target, and the like. Biologically compatible modifying groups may be used in embodiments of the invention as discussed above. For example, the modification of peptides may include the acylation or the acetylation of the amino-terminal end or the amidation, lipidation, methylation, or the esterification of the carboxy-terminal end. Both ends of the peptide may also be modified. Suitable modifying groups and methods of protecting polypeptides are well known in the art, and may be incorporated into peptides in accordance with the present invention.

Screening P9 and P10 Peptide Variants

The above-mentioned variants of pentapeptides P9 and P10 may be screened in vitro, ex vivo, or in vivo to determine their effects on melanin production and tyrosinase activity using one or more assays known in the art or those described in the materials and methods section below. The variants of pentapeptides P9 and P10 which increase the melanin production, tyrosinase activity, or both can be selected for use in compositions and treatment in accordance with the present invention.

In one implementation, an in vitro melanin content assay can be used to screen variants of P9 and P10. For example, melanoma cells (e.g., B16-F1 mouse melanoma cells) can be treated with P9, P10, or their variants at a suitable concentration (e.g., 300 micromolar) to induce melanin synthesis. The cells treated with peptides or untreated controls cells can be incubated for a suitable time period (e.g., 72 hours). Determinations of activating and toxic concentrations for the peptides can also be made using known methods and evaluated using techniques described in this application, and other methods known to those skilled in the art. Afterwards, control and treated cells can be harvested.

In an embodiment, extracellular melanin may be estimated spectrophotometrically based on its absorption of light at 475 nanometers. The extracellular melanin content of control cells and cells treated with P9, P10, or their variants can be compared. Variants of P9 and P10 that increase melanin production compared to the control and that increase melanin production to a level comparable to those of P9 and P10, respectively, may be selected for use in compositions and treatments in accordance with the present invention.

In another embodiment, intracellular melanin content may also be estimated. The control and treated cells (e.g., B16-F1 mouse melanoma cells) as described above can be collected by centrifugation, washed, re-centrifuged, and solubilized by treatment with 1 N NaOH solution as described in the materials and methods section below. Absorbance can be measured at 475 nanometers and compared to a standard curve prepared from standard dopa-melanin dissolved in the same solution. Melanin content per microgram cellular protein can be calculated and expressed as a percent control. The intracellular melanin content of the control can be compared to treated cells. Variants of P9 and P10 that increase intracellular melanin content compared to the control and that increase intracellular melanin content to a level comparable to those of P9 or P10, respectively, may be selected.

In the above described melanin content assays, melanin content induced by a P9 or P10 variant is considered "comparable" to that of P9 or P10, respectively, when melanin content of cells treated with a P9 or P10 variant is at least about 50, 60, 70, 80, 90, or 100 percent of the melanin content of cells treated with P9 or P10, respectively. These comparable P9 or P10 variants may be selected for use in compositions and treatments in accordance with the present invention.

In another implementation, tyrosinase activity of control and treated cells can be assayed to screen P9 and P10 variants that are suitable for use as compositions and treatments to increase melanin production in epidermis of a subject. In an embodiment, tyrosinase activity can be assayed as DOPA oxidase activity using a traditional or modified method. As described more in detail below in the materials and methods section, tyrosinase activity can be analyzed spectrophotometrically by following the oxidation of DOPA to DOPAchrome at 475 nanometers. The reaction mixture containing 100 microliter of freshly prepared substrate solution [0.1 percent L-DOPA in 0.1 mole per liter sodium phosphate (pH 6.8)] and 50 microliter of enzyme solution can be incubated at 37 degrees Celsius. The melanoma cells can be treated with a P9 or P10 variant at a selected concentration (e.g., about 0.03 millimolar to 3.00 millimolar). Absorbance change can be measured during the first 10 minutes of the reaction while the increase of the absorbance is linear, and corrections for auto-oxidation of L-DOPA in the controls can be made. Activities can be expressed as a percentage of control cells. P9 and P10 variants that increase tyrosinase activity, compared to untreated control, and P9 and P10 variants that increase tyrosinase activity to a level comparable to those of P9 and P10, respectively, may be selected.

In another embodiment, P9 and P10 variants can be screened using the assay of mushroom tyrosinase activity to determine which variant increases tyrosinase activity. As described more in detail in materials and methods section below, the mushroom tyrosinase activity can be determined in vitro using L-tyrosine as the substrate. The experiment can be conducted in a 96-well flat-bottomed plate. Each well can contain 80 microliters of 0.067 molar potassium phosphate buffer (pH 6.8), 40 microliters of 5 milligram per milliliter L-tyrosine dissolved in 0.067 molar potassium phosphate buffer (pH 6.8), 40 microliters of the different concentrations of P9, P10, or their variants dissolved in the same buffer, and 40 microliters of 480 units per milliliter mushroom tyrosinase solution. The final volume of each well can be 200 microliters, containing 1 microgram per microliter L-tyrosine, 96 units per milliliter tyrosinase and varying concentrations of P9, P10, or their variants, ranging from 30 micromolar to 1 millimolar. In the control wells, P9, P10, and their variants can be substituted with buffer solution and adjusted to a 200 microliter total volume. The assay mixture can be incubated at 37 degrees Celsius and optical density (OD), which correlates to the amount of dopachrome produced, can be measured periodically at 475 nanometers using a microplate reader (e.g., a Varioskan microplate reader from Thermo Electron Corporation). Using the mushroom tyrosinase assay, P9 and P10 variants that increase tyrosinase activity (e.g., at a concentration anywhere between about 0.03 millimolar to 3.00 milimolar), compared to untreated control, and those that have comparable tyrosinase activity as P9 or P10 can be selected.

In the above described tyrosinase assays, tyrosinase activity induced by a P9 or P10 variant is considered "comparable" to that of P9 or P10, respectively, when tyrosinase activity in cells treated with a P9 or P10 variant is at least about 50, 60, 70, 80, 90, or 100 percent of tyrosinase activity of cells treated with P9 or P10, respectively. These comparable P9 or P10 variants may be selected for use in compositions and treatments in accordance with the present invention.

In another implementation, P9 and P10 variants can be screened using a tissue model ex vivo. MelanoDerm™ Skin Model (MatTek Corporation, Ashland, Mass.) is a human skin tissue equivalent composed of keratinocytes and melanocytes. This model can be used to assess the effect of topically applied formulations on melanin accumulation within the tissue. Typical studies can usually involve 10-14 days of treatment. Pigmentation studies can also be conducted using keratinocyte-melanocyte co-cultures. In addition to assaying for changes in tissue melanin content, changes in pigmentation can also be assessed via histology using Fontana Masson staining P9 and P10 variants can be screened by topically applying a variant peptide onto MelanoDerm™ at a suitable concentration (e.g., about 0.03 millimolar to about 3.00 millimolar). P9 and P10 variants that increase pigmentation in MelanoDerm™, either visually or spectrophotometrically at 475 nanometers, compared to control can be selected for use in compositions and treatments in accordance with the present invention.

In another implementation, the effects of P9, P10, or their variants can be demonstrated on a skin sample. For example, 6 millimeter diameter biopsies can be taken from human skin samples. In an embodiment, human skin samples from normal subjects, patients with skin melanoma, patients with hypopigmentation disorder (e.g., vitiligo), and others can be biopsied. The biopsied samples are held in an ex vivo culture in the presence of a specific medium (1 gram per liter DMEM, Ham's F-12, SVF, and antibiotics) on inserts deposited on 6-well plates. The biopsies either receive or do not receive two applications daily of a selected peptide (e.g., P9, P10, or their variants) in a concentration of 1 percent, starting with a 50 parts-per-million (ppm) solution. The duration of the treatment can be 48 hours. The intensity of coloration of skin sections which received the selected peptide versus which did not receive the peptide can be compared visually or spectrophotometrically at 475 nanometers. P9 and P10 variants that increase pigmentation on the biopsied samples compared to untreated control can be selected for use in compositions and treatments in accordance with the present invention.

In another implementation, the effects of P9, P10, or their variants can be further tested for their skin-darkening activity on subjects. In this assay, healthy volunteers (comparable in age, sex, health, and like) are selected, and two spots in their brachial area (2.25 square centimeters each) can be tested. One spot is applied with the peptide composition and the control spot is applied with a composition without the selected peptide. The concentration of peptide in the composition can be tested at different concentrations (e.g., 0 weight to weight (w/w) percent (control), 2 weight to weight percent, 5 weight to weight percent, 8 weight to weight percent, or 20 weight to weight percent). The peptide for such assay may be prepared as described in U.S. Pat. No. 8,338,364, which is incorporated by reference. The skin-darkening effect can be determined by comparing the treated spot for melanogenesis against the control spot. The intensity or coloration of spot which received the selected peptide versus the control spot can be compared visually or spectrophotometrically 475 nanometer. P9 and P10 variants that increase pigmentation compared to untreated control can be selected for use in compositions and treatments in accordance with the present invention.

In the above described screening assays (e.g., MelanoDerm™, skin biopsies, volunteer subjects, and the like), P9 and P10 variants that increase pigmentation visually or spectrophotometrically, compared to untreated control, by at least 10, 20, 30, 40, 50, 60, 70, 80, 90, or 100 percent, or by at least 1.5-fold, 2.0-fold, and the like may be selected for use. Among these, the variants that produce the pigmentation level comparable to P9 or P10 may be further selected. The pigmentation level induced by a P9 or P10 variant is considered "comparable" to that of P9 or P10, respectively, when the pigmentation level of samples or subjects treated with a P9 or P10 variant is at least about 50, 60, 70, 80, 90, or 100 percent of the pigmentation level of samples or subjects treated with P9 or P10, respectively. These comparable P9 or P10 variants may be selected for use in compositions and treatments in accordance with the present invention.

In embodiments of the invention, any one or more of the above screening assays can be used to determine P9 and P10 variants that are suitable for use. For example, one melanin content assay and one tyrosinase assay may be selected for screening P9 and P10 variants. In certain embodiments, P9 and P10 variants may be further screened for their other biological effects on cells. For example, P9 and P10 variants' effects on cell viability and proliferation can be determined using the MTT proliferation and viability assays discussed in the materials and methods section below. Generally, P9 and P10 variants that do not affect cell viability and proliferation, like P9 and P10, may be selected for use. In another example, P9 and P10 variants' ability to allosterically activate tyrosinase may be screened using 6BH4 as described in the materials and methods section below. The term, "allosteric activation," can refer to increase in enzyme activity by binding of an effector at an allosteric site that affects binding or turnover at the catalytic site. The screening assays described in this application are merely exemplary, and other suitable screening assays known in the art may be used to screen P9 and P10 variants that can be used in embodiments of the present invention.

Compositions

In another aspect of the invention, the peptides in accordance with the present invention may be prepared and included in compositions. The compositions may include pharmaceutical compositions, dermatological compositions, cosmetic compositions, and others. These compositions (also referred to as formulations) include, as active ingredients, one or more peptides in accordance with the present invention that enhance melanin production or tyrosinase activity, or a combination of these. For example, pentapeptide P9 (SEQ ID NO: 1), pentapeptide P10 (SEQ ID NO: 2), their variants, or a combination of these can be incorporated as active ingredients. In an embodiment, a variant of P9 has an amino acid sequence essentially identical to YSSWY (SEQ ID NO: 1). In another embodiment, a variant of P10 has an amino acid sequence essentially identical to YRSRK (SEQ ID NO: 2). The compositions are formulated in a physiologically acceptable medium that includes substances (additives, carriers, or excipients, or a combination) that are biologically compatible with a body (e.g., a human body). Any suitable physiologically acceptable medium may be used as long as they do not pose toxicity, allergic reaction, instability, and the like.

In embodiments of the present invention, the term "carrier" can refer to compounds commonly used on the formulation of pharmaceutical compounds used to enhance stability, sterility and deliverability of the therapeutic tyrosinase activator. When the peptide delivery system is formulated as a solution or suspension, the delivery system is in an acceptable carrier, for example, an aqueous carrier. A variety of aqueous carriers may be used, e.g., water, buffered water, 0.8 percent saline, 0.3 percent glycine, hyaluronic acid and the like. These compositions may be sterilized by conventional, well-known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, and the like.

In some embodiments, the compositions may be formulated as dermatological or cosmetic compositions so that they can be applied topically. "Topical application" can refer to the application or spreading of the compositions or peptides according to the invention on the surface of the skin. They contain physiologically acceptable medium acceptable cosmetically, pharmaceutically, and dermatologically. The topical compositions may be formulated in various forms—solutions, gels, emulsions, suspensions, serums, lotions, skin cleansers, soaps, creams, sprays, semi-solids, solids, powders, and others.

In one implementation, peptides of the present invention can be formulated into topical compositions that contain a dermatologically acceptable carrier. The phrase "dermatologically-acceptable carrier", as used in this application, means that the carrier is suitable for topical application to the keratinous tissue, has good aesthetic properties, is compatible with the actives of the present invention and any other components, and will not cause any untoward safety or toxicity concerns. A safe and effective amount of carrier can be generally from about 50 percent to about 99.99 percent, or from about 80 percent to about 99.9 percent, or from about 90 percent to about 98 percent, or from about 90 percent to about 95 percent of the composition.

The carrier can be in a wide variety of forms. For example, emulsion carriers, including, but not limited to, oil-in-water, water-in-oil, water-in-oil-in-water, and oil-in-water-in-silicone emulsions, are useful in this application.

Emulsions according to the present invention generally contain a solution as described above and a lipid or oil. Lipids and oils may be derived from animals, plants, or petroleum and may be natural or synthetic (i.e., man-made). Preferred emulsions also contain a humectant, such as glycerin. Emulsions can further contain from about 0.01 percent to about 10 percent, or from about 0.1 percent to about 5 percent, of an emulsifier, based on the weight of the carrier. Emulsifiers may be nonionic, anionic or cationic. Suitable emulsifiers are disclosed in, for example, U.S. Pat. No. 3,755,560, issued Aug. 28, 1973, Dickert et al.; U.S. Pat. No. 4,421,769, issued Dec. 20, 1983, Dixon et al.; and McCutcheon's Detergents and Emulsifiers, North American Edition, pages 317-324 (1986). Examples of water-in-silicone and oil-in-emulsions are described in greater detail in U.S. patent publication 2006/0188462 by Bissett et al., published Aug. 24, 2006, entitled "Skin Care Compositions Containing a Sugar Amine."

The present peptides may also be formulated in liposomes. The present peptides may be contained in liposomes according to methods, for example, as described in U.S. Pat. No. 4,944,948 to Uster, et al., entitled "EGF/Liposome Gel Composition and Method." As described there, a high-viscosity aqueous dispersion of negatively charged liposomes may be prepared with liposome-entrapped peptide. The peptide-liposome composition is formed by suspending a lipid mixture typically containing equimolar amounts of neutral and negatively charged phospholipids and cholesterol in a low-conductivity aqueous medium containing peptide and a zwitterionic compound whose isoelectric point is between pH 5.5 and 8.5 to form a gel-like composition. Further exemplary guidance may be found in U.S. Pat. No. 4,485,054 to Mezei, et al., entitled "Method of Encapsulating Biologically Active Materials in Multilamellar Lipid Vesicles (MLV)."

In some embodiments, the compositions may further incorporate additional treatment additives that improve the appearance, disease state, or health of the skin as long as they do not negatively impact the effect of peptides according to the present invention. These include, for example, color additives, sunscreens, vitamins, anti-wrinkle agents, collagen, hydrating agents, antioxidants, caffeine, glycolic acids, hyaluronic acid, ceramide, copper, and others.

In some embodiments, the peptides in accordance with the present invention may be further included in a matrix. A matrix is a material or a structure which can be covered or embedded with peptides or compositions. Examples of a matrix include sponge, tissue, fabric, bandages, wrap, and the like. A matrix may assist the user in evenly applying the peptides and compositions on the user's skin.

In some embodiments, one or more peptides according to embodiments of the present invention may be formulated as a sunless tanning product. "A sunless tanning product" can refer to a product that can give the skin a tanned look without exposing it to harmful ultraviolet (UV) rays. Sunless tanning products can be formulated as lotions, sprays, solids, a matrix embedded with peptides, and the like. In some implementations, other active ingredients, such as color additives, may also be included in the sunless tanning product. The sunless tanning product may further include sunscreen agents, pigments, antioxidants, fragrance, and other ingredients typically used in a sunless tanning product.

In some embodiments, kits are provided. A kit may be used to perform a skin darkening procedure by increasing skin pigment production. A kit may include purified peptides having pentapeptide P9, pentapeptide P10, their variants, or a combination of these. The kit may include a dermatologically acceptable excipient or carrier. The kit may further comprise additional treatment product or device, such as a dermabrasion device, and directions for use. In certain embodiments, peptides and a carrier may be provided separately. In other embodiments, peptides and a carrier may be combined together to provide a composition suitable for use (e.g., topical application).

In another implementation, the present peptides may be prepared as an oral or injectable formulation. The pH of the injectable formulation is important, especially in regard to safety and comfort during injection, and especially if the preparation is supplied in a liquid formulation. A suitable formulation may contain preservatives, such as sodium benzoate, methylparaben and propylparaben, and the like, and may have a pH of 6.8-8.0 at 25 degrees Celsius. The pH can be maintained by a buffer. Suitable buffering agents include acetate buffers, 2-amino-2-methyl-1-propanol, glycine buffers, phosphate buffers, (tris-hydroxymethyl-aminomethane) (TRIS) buffers, (2-N-morpholino-ethanesulfonic acid), and the like. The formulation will typically also comprise a carrier as defined above. Injectable formulations are suitable for use in the treatment or prevention of melanomas and other cancers. These formulations are useful with melanocytes not approachable by topical application, such as melanocytes found in nonkeratinous tissue. Melanocytes are found in the basal layer of the epidermis as well as in hair follicles, the retina, uveal tract, and leptomeninges. These cells are the sites of origin of melanoma. Regarding oral formulations, an exemplary formulation may be found in U.S. patent publication 2007/0134279.

The present peptides may be used alone or in combination with each other. They may also be used in combination with other active ingredients. Examples of other active ingredients include substrates for tyrosinase, such as tyrosine or L-DOPA, IBMX (3-isobutyl-1-methylxanthine), scorparone, retinoic acid, and others. In some embodiments, topical corticosteroid may be combined with the present peptides to improve results. They may be delivered by liposomes or other transdermal delivery mechanism, such as disruptive devices. A fatty acid chain may be conjugated to the C-terminus or N-terminus of the peptide to promote non-liposomal based delivery via lipid partition into the stratum corneum.

Lipid peptide formulations of the present peptides are further described in U.S. Pat. No. 6,287,590 to Dasseux, issued Sep. 11, 2001, entitled "Peptide/Lipid Complex Formation by Co-lyophilization"; U.S. Pat. No. 5,543,389 to Yatvin, et al., issued Aug. 6, 1996, entitled "Covalent Polar Lipid-Peptide Conjugates for Use in Salves"; and other references.

The effective amount of active ingredients may correspond to the quantity necessary to achieve the desired pigmentation result. According to one embodiment, the peptides can be present in the compositions at a concentration of between about 0.0001 and about 50 percent by weight, between about 0.001 and about 10 percent by weight, or between about 0.01 and about 1 percent by weight, with respect to the total weight of the final composition. The calculations necessary to determine the appropriate concentration of peptides for treatment can be routinely made by those of ordinary skill in the art and is within the scope of tasks routinely performed by them without undue experimentation. Suitable concentrations may be ascertained through use of the established assays for determining dosages utilized in conjunction with appropriate dose-response data.

In embodiments of the present invention, the term "therapeutically effective amount" is intended to mean the amount of drug sufficient to produce a tyrosinase activating effect applied to a melanocyte, resulting in increase or enhancement of the production of melanin. These may be determined by methods known in the art, and can typically range from about 1 to 20,000 milligram per human adult, or about 10 to 10,000 milligrams, or about 20 to 5,000 milligrams of the activating agent per application, depending upon the formulation chosen, and whether the tissue, such as the skin or mucous membrane is the site of action. The only upper limit on the amount of drug in the composition is that the preparation is substantially free of crystals of activating agent and the amount of solvent used is not sufficient to undesirably affect the properties of the finite composition allowing it to adhere to the desired site of application. Thus, the single ingredient activating peptide contains a therapeutically effective amount of activating agent within the foregoing range.

The concentration of peptide has been found experimentally to be suitable when extrapolated from the EC 50. The term "EC 50," as is understood in the art, can refer to the concentration of tyrosinase activator peptide required to effect 50 percent activation of tyrosinase activity, as conducted in an in vitro assay; a values of "less than" a certain concentration includes EC 50 values at lower concentrations. The term about may encompass plus or minus 10 percent variation, and variations resulting from different reagents, experimental conditions, and the like. In vitro determination of EC 50 using a purified tyrosinase preparation (e.g., mushroom tyrosinase) can be useful in determining a clinical dose.

In general, it is suggested that concentrations above two times EC 50 would be appropriate for prescription use; below about two times EC 50 would be suitable for over the counter use. However, formulations may contain up to about 100 times EC 50, to allow for lack of skin uptake or other losses. In certain embodiments, at twice EC 50, 95 percent tyrosinase activation may be achieved.

In embodiments of the present invention, the dose that produce half the maximum response may be within about 300 micromolar range. This was the range which increased melanin content about 48 percent (e.g., see FIG. 3). Thus, EC 50 was well below cytotoxic levels which are higher than 10 micromolar. If EC 50 of peptide P9 and P10 were about 300 micromolar range (which cause 50 percent increase in enzyme activity and cause 170 and 180 percent increase in melanin in certain embodiments), then in one ounce or 30-milligram tube, 6.3 milligrams of peptide P9 or P10 can provide an EC 50 response. In certain embodiments, if twice the EC 50 response is desired, the formulation may contain about 12.6 milligrams (0.0126 grams) of peptide P9 or P10.

An exemplary composition that includes peptide P9 or P10 are prepared and is presented in table D below.

TABLE D

| Ingredient Name | Acceptable Range | Preferred Range |
|---|---|---|
| 1. Water | 1.00-90.00% | 30.00-70.00% |
| 2. Aloe barbadensis leaf juice | 1.00-90.00% | 5.00-60.00% |
| 3. Caprylic/capric triglyceride | 1.00-15.00% | 5.00-10.00% |
| 4. Pentylene glycol | 0.50-10.00% | 1.00-5.00% |
| 5. Diglycerin | 0.50-20.00% | 1.00-10.00% |
| 6. Bis-ethoxydiglycol cyclohexane 1,4-dicarboxylate | 0.50-3.00% | 1.00-2.00% |
| 7. Dimethicone | 0.50-10.00% | 1.00-5.00% |
| 8. Ethyl ascorbate | 0.10-10.00% | 1.00-5.00% |
| 9. Sodium hyaluronate | 0.50-90.00% | 5.00-20.00% |
| 10. Sodium pca | 0.50-20.00% | 1.00-5.00% |
| 11. Cetearyl alcohol | 0.50-5.00% | 1.00-3.00% |

TABLE D-continued

| Ingredient Name | Acceptable Range | Preferred Range |
|---|---|---|
| 12. Dicetyl phosphate | 0.50-5.00% | 0.50-3.00% |
| 13. Ceteth-10 phosphate | 0.50-5.00% | 0.50-3.00% |
| 14. Squalane | 0.50-10.00% | 1.00-5.00% |
| 15. Sclerotium gum | 0.20-4.00% | 0.50-2.00% |
| 16. Pentapeptide p9 or p10 | 0.01-50% | 0.1-10.00% |
| 17. Butylene glycol | 1.00-30.00% | 3.00-10.00% |
| 18. Panthenol | 0.10-5.00% | 0.50-2.00% |
| 19. Allantoin | 0.01-1.00% | 0.10-0.50% |
| 20. Tetrasodium edta | 0.05-2.00% | 0.10-0.50% |
| 21. Chlorphenesin | 0.10-1.00% | 0.10-0.50% |
| 22. Caprylyl glycol | 0.10-2.00% | 0.50-1.00% |
| 23. Phenoxyethanol | 0.30-2.00% | 0.50-1.00% |

The concentration as well as the quantity of activating peptide (e.g., P9 or P10) per unit area, namely per square or cubic centimeter can be varied independently in order to achieve the desired effect. Higher concentrations of activating peptide base contained in a dosage form of decreased thickness will result in an application of short duration. High concentrations of the activating peptide base contained in a dosage form of increased thickness (higher mg of activating peptide per square or cubic centimeter) will result in potent activator with fast onset and long duration. Low concentrations of the activating peptide base in a dosage form of decreased thickness will result in mild activation with longer onset and short duration. Low concentrations of the activating peptide contained in a dosage form of increased thickness will have mild activation with longer onset and longer duration. As shown in the above explanation, the ability to vary the concentration of activating peptide from very low (about 1 percent) to high (40 percent or higher) of the total composition, when combined with the ability to coat thin (about 0.001 inches) or thick (about 0.500 or more inches) enables the practitioner of the invention to vary the dosage of the system as needed for particular anatomical sites of interest.

As a general rule, in the case of a given tissue, e.g., the subepithelial layer, the peptide drug selected, the concentration and thickness and the duration of the application is determined based upon the peptide's ability to penetrate the tissue, for example the basal layer of the epidermis or mucosa, and to be at peak effectiveness within about 2 to 30 minutes. The duration of the effect of the activating peptide on the tissue, for example the epidermis can range between about 2 to 240 minutes, depending on the agent selected, the concentration of the activating peptide and the thickness of application. Longer or shorter durations can also be selected dependent on need, as will be apparent to one skilled in the art.

Treatments with Compositions

In another aspect, embodiments of the present invention relate to methods of increasing melanin production in epidermis of a subject. The epidermis is the outer layer of the two main layers of cells that make up the skin. Without wishing to be bound by any one theory, peptides in accordance with the present invention may enhance production of melanin in the skin by activating tyrosinase enzyme. In an embodiment, the subject may be treated with pentapeptide P9, pentapeptide P10, any variant of pentapeptide P9 or P10, or any combination of these. In an embodiment, a variant of pentapeptide P9 has an amino acid sequence essentially identical to YSSWY (SEQ ID NO: 1). In another embodiment, a variant of pentapeptide P10 has an amino acid sequence essentially identical to YRSRK (SEQ ID NO: 2).

In one implementation, the present invention relates to treating vitiligo, piebaldism, albinism, and other hypopigmentation disorders using peptides or compositions described in the present invention. Hypopigmentation is the loss of skin color. It can be caused by melanin depletion. The subjects with hypopigmentation disorders can be systematically, orally, parenterally, or topically administered with peptides or compositions containing the peptides to increase pigment production in epidermis of the subjects.

As used in this application, "treating" describes the management and care of a patient for the purpose of combating a disease, condition, or disorder and includes the administration of a peptide or composition of the present invention to prevent the onset of the symptoms, alleviating the symptoms, or eliminating the disease, condition or disorder. Treatment can be continued as long as symptoms and/or pathology improve. Treatment can be performed several times a day, daily, weekly, or for any suitable intervals and durations until the symptoms and/or pathology improve.

In another implementation, a method for pigmenting (coloring) skin grafts in vitro and in vivo is provided by applying the present peptides and/or compositions on the skin grafts (autografts or allografts) Skin grafting is used for extensive wounds that are difficult to suture or for wounds that will produce prominent scars. Sometimes the pigmentation level of a skin graft may not match the pigmentation level at the recipient site. The skin grafts may be treated with peptides and compositions in accordance with the present invention at a suitable concentration and duration so that the pigmentation level of the skin grafts can be matched with that of the recipient site.

In another implementation, the method relates to increasing melanin production in the epidermis of a subject with the present peptides and compositions to reduce symptoms of photosensitivity disorders such as erythropoietic protoporphyria (EPP), solar urticaria (SU) and polymorphic light eruption (PLE), which lack fully effective treatments and result in significant morbidity.

In another implementation, the melanin production can be enhanced in the skin to protect against skin cancers—either melanoma type or nonmelanoma type using one or more peptides or compositions, or a combination, in accordance with the present invention. Melanoma is a type of skin cancer that begins in the skin's pigment-producing cells, called melanocytes. These cells make melanin. Melanoma is the deadliest form of cancer, but it is not the most common. Nonmelanoma type cancers, such as basal cell and squamous cell skin cancers occur more often than melanoma. The peptides and compositions in accordance with the present invention can be used as a preventative measure of skin cancer by increasing pigmentation in epidermis of the subject.

In specific implementations, the peptides and compositions according to the present invention may be applied in conjunction with dermabrasion or any other suitable techniques to improve permeation of peptides into the skin. Dermabrasion is a cosmetic medical procedure in which the surface of the skin is removed by abrasion (sanding). The peptides can be administered as part of a solution delivered during microdermabrasion. The details on the method of microdermabrasion treatment can be found in U.S. Pat. No. 6,695,853, which is incorporated by reference. The present peptides can also be used with microneedle treatment, electroporation, iontophoresis, laser treatments, and/or other techniques, which are described in U.S. Pat. No. 7,902,329 and U.S. Pat. No. 8,026,208, which are incorporated by reference.

The following examples describe and demonstrate the effectiveness of pentapeptides P9 and P10.

EXAMPLES

Materials and Methods

Reagents.

Mushroom tyrosinase, L-tyrosine, L-3,4-dihydroxyphenylalanine (L-DOPA), 3-isobutyl-1-methylxanthine (IBMX), Scoparone, (6R)-L-erythro-5,6,7,8-tetrahydrobiopterin (6BH4), and α-Melanocyte Stimulating Hormone (α-MSH) were used. Oligopeptides P9 and P10, as displayed in FIGS. 1A-1B, were synthesized using solid-phase FMOC chemistry.

Cell Culture.

B16-F1 mouse melanoma cells (CRL-6323) were obtained and cultured in DMEM containing 10 percent fetal bovine serum, 100 units per milliliter (U/mL) penicillin, 0.1 mg/mL streptomycin, and 0.25 microgram per milliliter (μg/mL) amphotericin B at 37 degrees Celsius in a humidified 95 percent air/5 percent $CO_2$ incubator. Drug treatment began 24 hours after seeding. Cells were harvested 72 hours later and melanin content and tyrosinase activity determined in triplicate.

Melanin Content Measurement.

Extracellular melanin was estimated spectro-photometrically based on its absorption of light at 475 nanometers. After 72 hours treatment period, medium was collected and centrifuged (800×g for 10 minutes) and absorbance read at 475 nanometers. For intracellular melanin content, cells were collected by centrifugation and resuspended in PBS. Aliquots were removed for cell counting and protein estimation. To the remaining suspension, an equal volume of ethanol:ether (1:1 volume to volume) was added in order to remove opaque substances other than melanin which is not soluble in ethanol/ether (see, for example, Oikawa et al., *Yale J. Biol. Med.*, 1973, 46: 500-507). After further centrifugation at 3000×g for 5 minutes, the precipitate was solubilized by treatment with 1 milliliter of 1 N NaOH solution at 80 degrees Celsius for 30 minutes in capped tubes. The absorbance was measured at 475 nanometers and compared to a standard curve prepared from standard dopamelanin dissolved in the same solution. Melanin content per microgram (μg) cellular protein was calculated and expressed as a percentage of control.

Assay of B16 Tyrosinase Activity.

Tyrosinase activity was assayed as DOPA oxidase activity. This can be according to traditional or modified assaying methods (see, for example, Yang et al., *Acta Pharmacol. Sin.* 2006, 27: 1467-1473). Cells were washed twice with PBS and lysed with 20 nanomoles per liter (mmol/L) Tris-0.1 percent Triton X-100 (pH 7.5). Tyrosinase activity was analyzed spectrophotometrically by following the oxidation of DOPA to DOPAchrome at 475 nanometers. The reaction mixture containing 100 microliter (μL) of freshly prepared substrate solution [0.1 percent L-DOPA in 0.1 mol/L sodium phosphate (pH 6.8)] and 50 microliters (μL) of enzyme solution was incubated at 37 degrees Celsius. Absorbance change was measured during the first 10 minutes of the reaction while the increase of the absorbance was linear, and corrections for auto-oxidation of L-DOPA in the controls were made. Activities were expressed as a percentage of control cells.

Assay of Mushroom Tyrosinase Activity.

The effect of pentapeptides P9 and P10 on mushroom tyrosinase activity was determined in vitro using L-tyrosine as the substrate (see, for example, Piao et al., *Chem. Pharm. Bull.* (Tokyo), 2002, 50: 309-311). The experiment was conducted in a 96-well flat-bottomed plate. Each well contained 80 microliters of 0.067 molar potassium phosphate buffer (pH 6.8), 40 microliters of 5 milligrams per milliliter L-tyrosine dissolved in 0.067 molar potassium phosphate buffer (pH 6.8), 40 microliters of the different concentrations of P9 or P10 dissolved in the same buffer, and 40 microliters of 480 units per milliliter mushroom tyrosinase solution. The final volume of each well was 200 microliters, containing 1 microgram per milliliter L-tyrosine, 96 units per milliliter tyrosinase and varying concentrations of P9 or P10, ranging from 30 micromolar to 1 millimolar. In the control wells, P9 and P10 were substituted with buffer solution and adjusted to a 200 microliters total volume. The assay mixture was incubated at 37 degrees Celsius and optical density (OD), which correlates to the amount of dopachrome produced, was measured periodically at 475 nanometers using a microplate reader (e.g., a Varioskan microplate reader from Thermo Electron Corporation).

Allosteric Activation of Tyrosinase.

To investigate the mechanism by which P9 and P10 exert their stimulatory effect on tyrosinase, 6BH4, an allosteric inhibitor of tyrosinase, was used in an experiment. In a 96-well plate, control wells containing substrate L-tyrosine, purified mushroom tyrosinase, and PBS (pH 6.8) were incubated at 37 degrees Celsius and periodically read at 475 nanometers. After 6 minutes, 20 micromolar 6BH4 was added to all wells except controls. At minute 12, the other triplicate wells received one of the following reagents: 20 micromolar of α-MSH, 100 micromolar of P4, P9, or P10, or 200 micromolar L-tyrosine.

MTT Proliferation and Viability Assays.

Proliferation rates were determined using a general cell proliferation kit (e.g., TACS® MTT Cell Proliferation Kit from R&D systems). Cells were plated at 2.5×10E4 per well in 96-well plates in a humidified atmosphere with 5 percent CO2 at 37 degrees Celsius. Twenty-four hours after plating, test samples were added and cultures were incubated for an additional 72 hours. The remainder of the procedure was performed following the manufacturer's protocol.

Statistical Analysis.

Each experiment was performed in triplicate and repeated a minimum of three independent times. The results were averaged and standard errors of the mean were calculated for all conditions. Values were expressed as means±SEM. All data were examined for statistical significance with student's t test, one-way ANOVA and repeated measured ANOVA.

Example 1

P9 and P10 Amino Acid Sequences

FIGS. 1A-1B show the amino acid sequences and structures of two novel oligopeptides. FIG. 1A shows the sequence and structure of pentapeptide P9, and FIG. 1B shows the sequence and structure of pentapeptide P10. As described in the materials and methods section above, these peptides were synthesized using solid-phase FMOC chemistry.

Example 2

Pentapeptides P9 and P10 Increase Melanin Content and Tyrosinase Activity

Figure 2A:
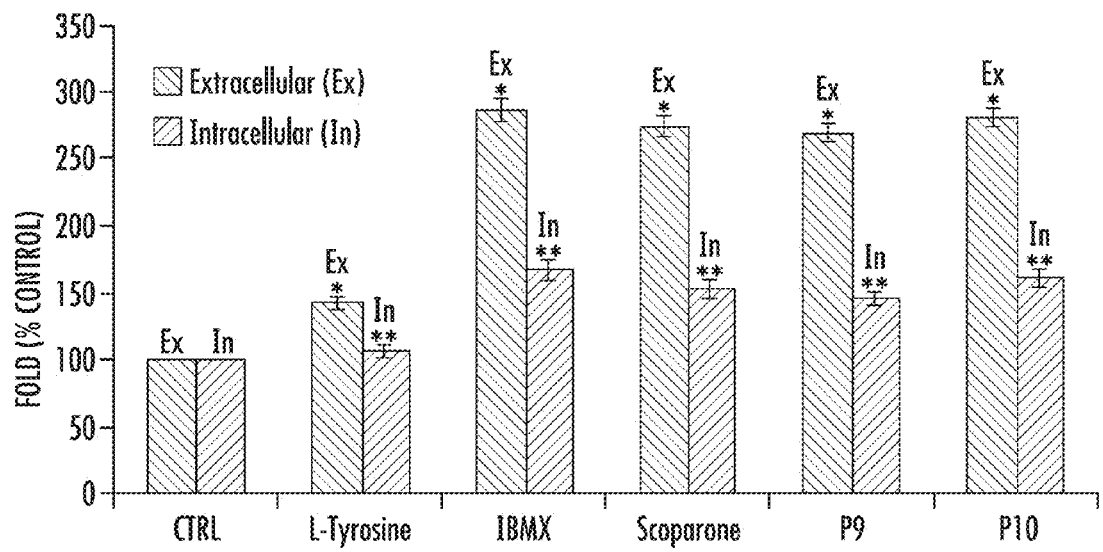
FIG. 2A shows a graph indicating the effect of P9 and P10 on extracellular and intracellular melanin content.
Figure 2B:
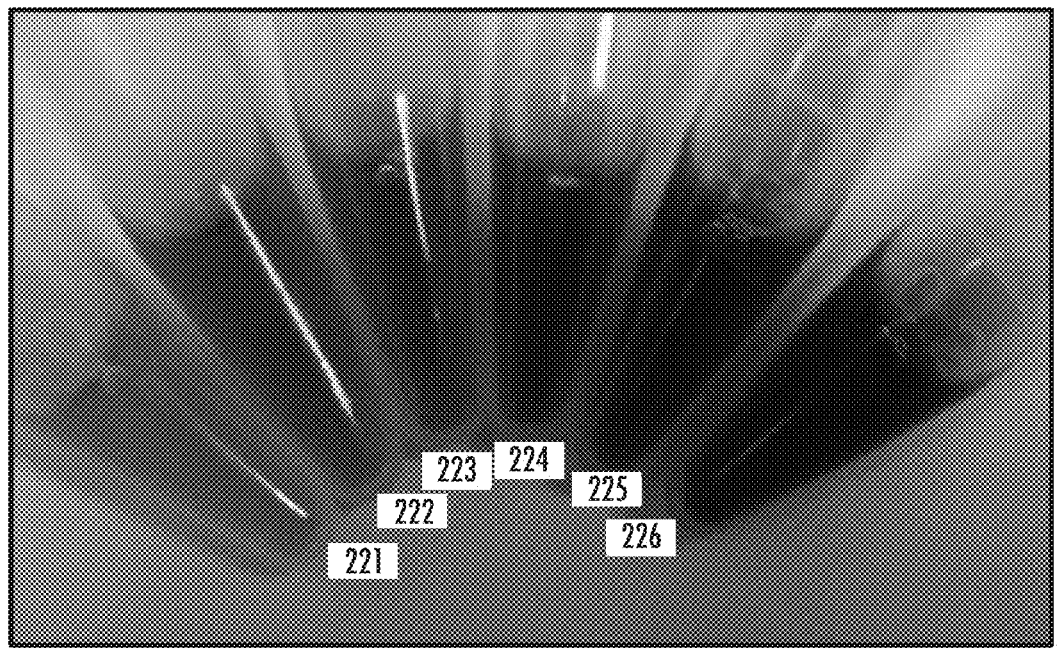
FIG. 2B shows a picture of the effect of treatment on the appearance of cell suspension after a 72 hour incubation period.

FIGS. 2A-2B show the effect of P9 and P10 on extracellular and intracellular melanin content. FIG. 2A shows results of the effects L-Tyrosine, IBMX, Scoparone, P9, and 910 versus a control on extracellular (left side bar of each agent, indicated on the graph as Ex) and intracellular (right side bar of each agent, indicated on the graph as In) melanin content. In a specific embodiment, general materials and methods include 3×10E5 B16 cells per well incubated for 72 hours. Control wells had media only. Other treatments were 600 micromolar L-tyrosine; 50 microgram per milliliter scoparone; 300 micromolar IBMX; 300 micromolar P9; and 300 micromolar P10. Data are expressed as a percentage of the control and are mean±SEM of three separate experiments and analyzed by one-way ANOVA. On the graph, for the bar corresponding to extracellular data (indicated by "*"), P<0.01 versus extracellular control, and for the second bar corresponding to intracellular data (indicated by "**"), P<0.01 versus intracellular control.

FIG. 2B shows a picture of the effect of treatment on the appearance of cell suspension after a 72 hour incubation period. The suspensions are labeled tubes 221-226. For tube 221, the cell suspension includes the control, as indicated in the graph of FIG. 2A. Tube 222 includes the cell suspension with 600 micromolar L-tyrosine, as indicated in the graph of FIG. 2A. Tube 223 includes the cell suspension with 300 micromolar IBMX, as indicated in the graph of FIG. 2A. Tube 224 includes the cell suspension with 50 microgram per milliliter scoparone, as indicated in the graph of FIG. 2A. Tube 225 includes the cell suspension with 300 micromolar P9, as indicated in the graph of FIG. 2A. Tube 226 includes the cell suspension with 300 micromolar P10, as indicated in the graph of FIG. 2A. From tube 221 to tube 226, there is an increase in the darkness of color (pigmentation) of the cell suspension, with tube 221 (with the control) having the lightest cell suspension, and tubes 225 (with P9) and 226 (with P10) having the darkest cell suspension.

Pentapeptides P9 and P10 increased the intracellular and extracellular melanin content of B16 melanoma cells in a dose-dependent manner (see FIG. 3) similar to positive controls (IBMX and scoparone). As shown in FIG. 2A, 300 micromolar for P9 and P10 were used, compared to 300 micromolar IBMX and 50 microgram per milliliter of scoparone, to compensate for potential peptide degradation during the 72 hours incubation period. After 72 hours incubation with 300 micromolar IBMX, the extracellular melanin content increased by 187±9 percent compared to an increase by 170±6 percent and 181±7 percent for P9 and P10, respectively.

Intracellular melanin content increased by 53±6.9 percent and 67±6 percent for scoparone and IBMX, respectively, versus 47±6 percent and 62±6 percent for 300 micromolar P9 and P10, respectively. Since P9 and P10 both contain L-tyrosine residues, their degradation may increase the concentration of substrate available for tyrosinase thereby increasing melanin content. To assess this possibility, the cells were treated with 600 micromolar L-tyrosine, the equivalent L-tyrosine concentration in 300 micromolar P9, but there was a minimal increase in intracellular melanin content (7±3 percent) although extracellular melanin content increased 43±5 percent relative to control.

These pentapeptides can enhance melanogenesis in a dose-dependent manner comparable to IBMX, scoparone, and α-MSH. However, unlike these agents which increase melanin content by enhancing cAMP-dependent transcription of tyrosinase and tyrosinase related proteins, P9 and P10 effects occurred in a cell-free system, as shown in FIGS. 2A-2B, suggesting a direct enzyme effect.

Example 3

P9 and P10 Increase B16 Mushroom Tyrosinase Activity

Figure 3:
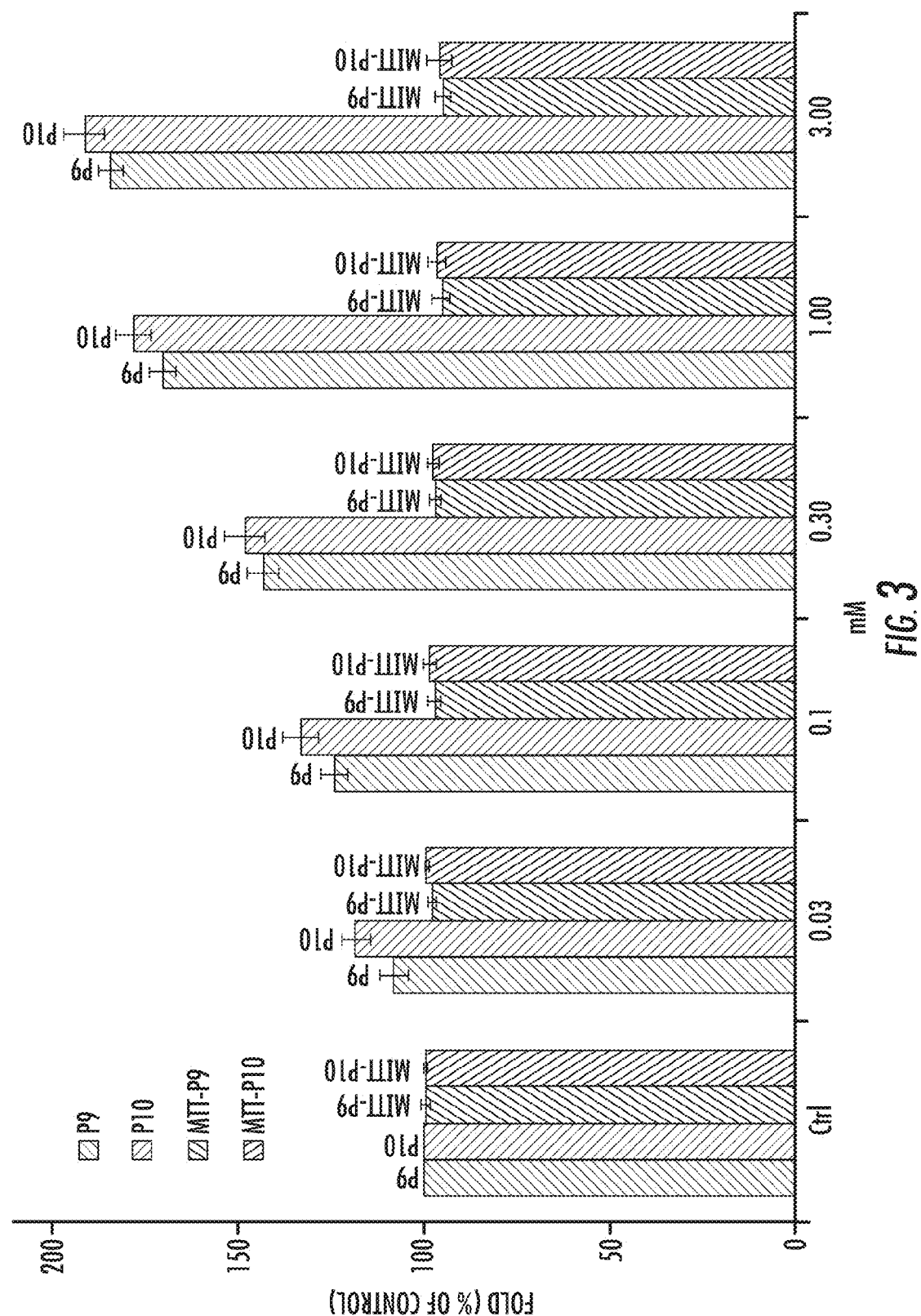
FIG. 3 shows a graph indicating the effect of P9 and P10 on tyrosinase activity and cell proliferation rates of B16 cells after 72 hours of incubation with various concentrations.

FIG. 3 shows the effect of P9 and P10 on tyrosinase activity and cell proliferation rates of B16 cells after 72 hours of incubation with various concentrations. For each concentration, the first bar on the graph for each concentration shows the effect of P9 (indicated by "P9"). The second bar for each concentration shows the effect of P10 (indicated as "P10"). The third bar for each concentration shows the effect of MTT-P9 (indicated as "MTT-P9"). The fourth bar for each concentration shows the effect of MTT-P10 (indicated as "MTT-P10").

For the tyrosinase activity, the reaction mixture containing 100 microliter of freshly prepared substrate solution [0.1 percent L-DOPA in 0.1 moles per liter sodium phosphate (pH 6.8)] and 50 microliters of enzyme solution was incubated at 37 degrees Celsius. The absorbance change was measured during the first 10 minutes of the reaction while the increase of the absorbance was linear, and corrections for auto-oxidation of L-DOPA in the controls were made. Activities were expressed as a percentage of the control cells. MTT was performed following the manufacturer's protocol. Data are expressed as a percentage of control and are mean±SEM of three separate experiments. On the graph, the "*" indicates that P<0.01 versus the control by repeated measured ANOVA.

As shown in FIG. 3, B16 tyrosinase activity increased by 38±4 percent and 48±5 percent and by 84±3 percent at 300 micromolar and 91±6 percent at 3 millimolar for P9 and P10, respectively. At concentrations as high as 10 millimolar, proliferation rate was 94±2 percent and 95±2 percent for P9 and P10, respectively.

Example 4

P9 and P10 Increase Tyrosinase Activity in a Dose-Dependent Manner

Figure 4A:
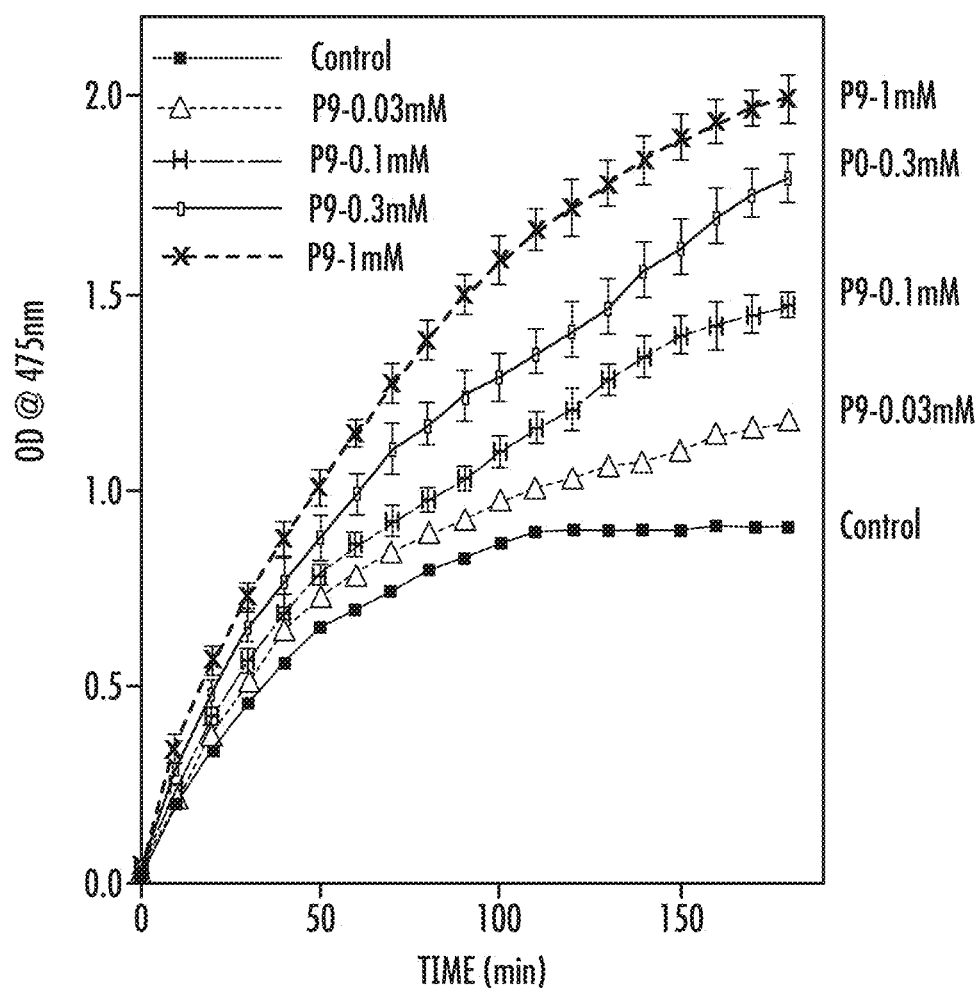
FIG. 4A shows a dose response curve for peptide P9.
Figure 4B:
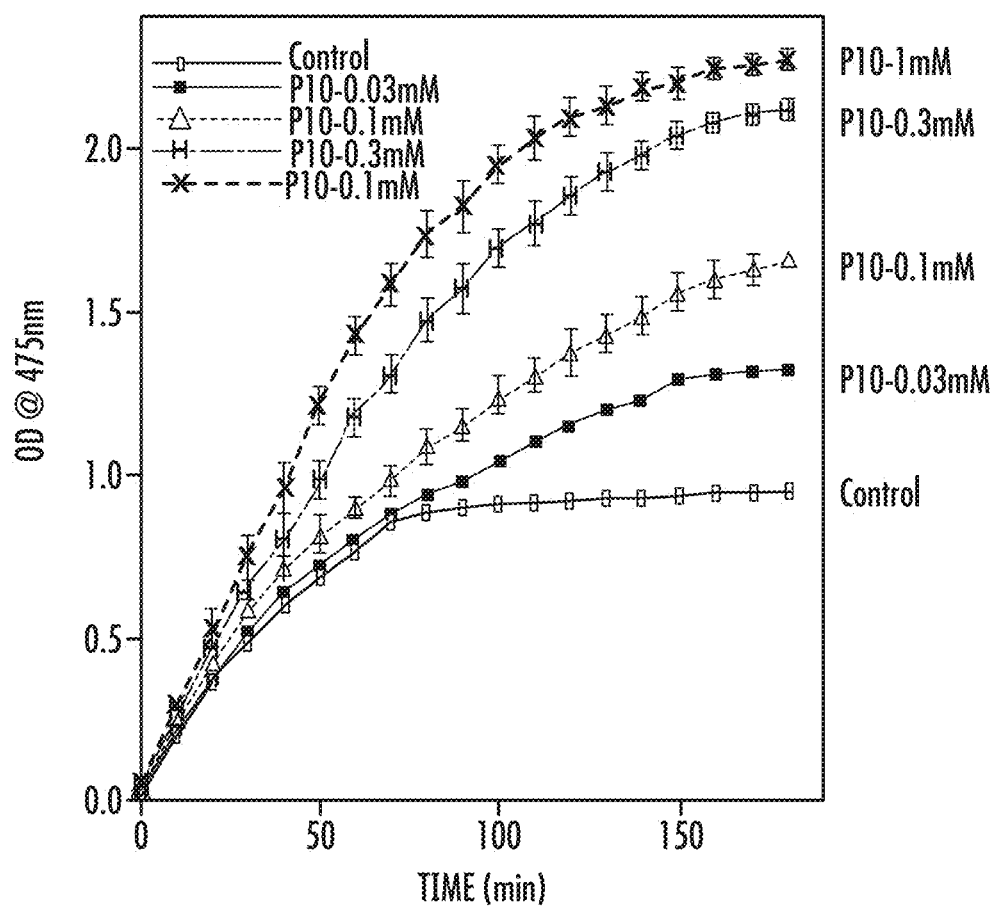
FIG. 4B shows a dose response curve for peptide P10.

FIGS. 4A and 4B show mushroom tyrosinase activity increased by 123±4 percent and 156±4 percent at 1 millimolar P9 and P10, respectively. FIG. 4A shows dose response curves for peptide P9, and FIG. 4B shows does response curves for peptide P10. In the control wells, the reaction mix included purified mushroom tyrosinase, PBS (pH 6.8) and substrate L-tyrosine. In the other triplicate wells, P9 or P10 were added at various concentrations. The reaction was incubated at 37 degrees Celsius and the plate was read periodically at 475 nanometers.

Data represents the means±SEM of three independent tests, each performed in triplicates. Dopachrome formation increased by 100±3 percent and 134±3 percent at 300 micromolar and by 28±3 percent and 45±3 percent at 30 micromolar for P9 and P10, respectively.

Example 5

P9 and P10 Allosterically Activate Tyrosinase

Figure 5:
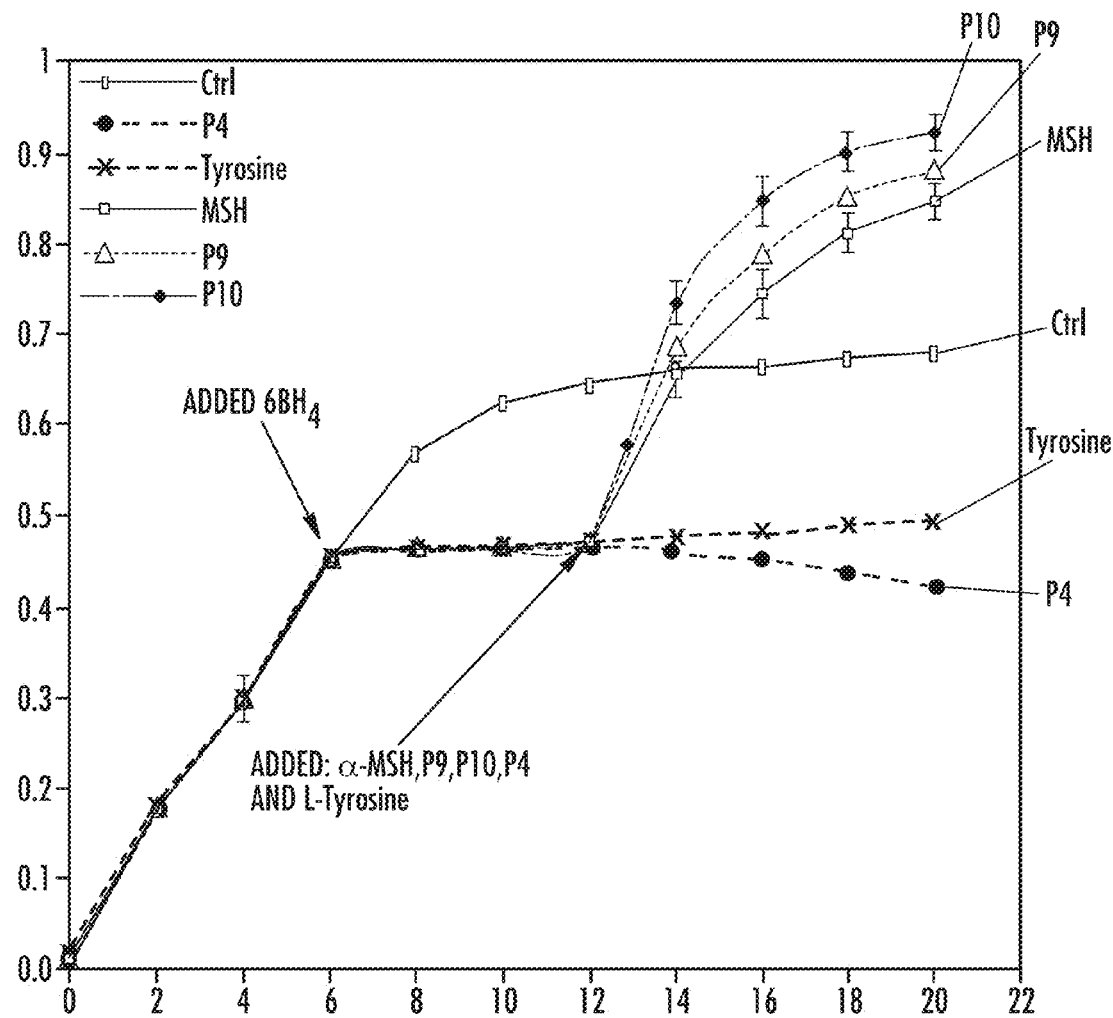
FIG. 5 shows a dose response curve for allosteric activation of tyrosinase after inhibition by 6BH4.

FIG. 5 shows a dose response curve for allosteric activation of tyrosinase after inhibition by 6BH4. In a 96-well plate the control wells contained substrate L-tyrosine, purified mushroom tyrosinase and PBS (pH 6.8). The plate was incubated at 37 degrees Celsius and periodically read at 475 nanometers. After six minutes, 6BH4 was added to all wells except the control triplicate. At minute 12, the other triplicate wells received one of the following reagents: 10 micromolar of α-MSH, 100 micromolar of P4, P9 or P10, and 200 micromolar L-tyrosine. Data shown are mean±SEM of three independent runs.

To assess whether P9 and P10 exerted their stimulatory effect via allosteric activation, 6BH4 was added at 6 minutes post-incubation and then the tyrosinase activity was observed for an additional 6 minutes. FIG. 5 shows that tyrosinase activity was inhibited completely by 6BH4. At minute 12, addition of P9, P10, or α-MSH reactivated the enzyme. On the other hand, neither the addition of P4 nor L-tyrosine reversed 6BH4's inhibition. Without wishing to be bound by any one theory, this indicates that P9 and P10 can allosterically activate tyrosinase.

As shown in FIG. 5, the data showed that P9 and P10, but not scoparone or IBMX, were capable of reversing (6R)-L-erythro-5,6,7,8-tetrahydrobiopterin (6BH4)-dependent tyrosinase inhibition. Similarly, neither L-tyrosine nor P4, a decapeptide tyrosinase inhibitor, reversed 6BH4 effects. P4 is comprised of P9 and P10 (see sequence in FIGS. 1A-1B). The absence of a stimulatory effect suggested that degradation and liberation of L-tyrosine residues cannot explain the effect of P9 and P10. Moreover, the data supports that the binding site is not in the catalytic pocket, and the mechanism of action of P9 and P10 is distinct from that of P4.

As shown in FIG. 5, P9, P10, and α-Melanocyte Stimulating Hormone (α-MSH) were able to reverse the inhibition and activate the enzyme. In fact, not only did they reactivate the enzyme, but they also increased its activity to levels exceeding the control, as shown in FIG. 5. This α-MSH data shows an ability to increase tyrosinase activity without increasing its synthesis levels.

α-MSH can exert pleiotropic effects on melanogenesis, including allosteric activation. 6BH4 is the natural cofactor for tyrosine hydroxylase and other amino acid hydroxylases. 6BH4 regulates tyrosinase via uncompetitive allosteric inhibition. The 6BH4/tyrosinase inhibitor complex can be reactivated by α-MSH. Based on results from the present invention, P9 and P10 can be allosteric activators of tyrosinase.

As illustrated in the examples above, pentapeptides P9 and P10 significantly increase melanin content in a dose-dependent manner comparable to the positive controls, IBMX, scoparone, and α-MSH. However, unlike IBMX and scoparone, but similar to α-MSH, P9 and P10 were able to reverse 6BH4-dependent tyrosinase inhibition. Not wishing to be bound by any one theory, pentapeptides P9 and P10 can allosterically activate tyrosinase and consequently enhance epidermal melanin synthesis. In embodiments of the present invention, the present peptides also do not affect cell proliferation or viability compared to untreated controls.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. A peptide consisting of SEQ ID NO: 1.

2. A composition comprising a first peptide consisting of SEQ ID NO: 1.

3. The composition of claim 2 further comprising a second peptide having at least 60% homology to YSSWY (SEQ ID NO: 1) or YRSRK (SEQ ID NO:2).

4. The composition of claim 3 wherein the second peptide consists of SEQ ID NO: 2.

5. The peptide of claim 1 wherein the peptide is modified by a modifying group, the modifying group being either an acylation or an acetylation of an amino-terminal end, or amidation, lipidation, methylation, or an esterification of a carboxy-terminal end, or both.

6. The composition of claim 2 wherein the first peptide is modified by a modifying group, the modifying group being either an acylation or an acetylation of an amino-terminal end, or amidation, lipidation, methylation, or an esterification of a carboxy-terminal end, or both.

7. The composition of claim 3 wherein the first peptide and/or the second peptide are modified by a modifying group, the modifying group being either an acylation or an acetylation of an amino-terminal end, or amidation, lipidation, methylation, or an esterification of a carboxy-terminal end, or both.

8. A method of treating a subject by increasing melanin production in skin to reduce symptoms of a photosensitivity disorder, the method comprising administering to a subject in need thereof a composition comprising an effective amount of one or more peptides, wherein the one or more peptides have an amino acid sequence at least 60% homologous to one of:

YSSWY, (SEQ ID NO: 1)
or
YRSRK, (SEQ ID NO: 2)

wherein the one or more peptides activate tyrosinase to increase melanin production in an epidermis of the subject.

9. A method of treating a subject in need of increasing melanin production in skin to protect against skin cancers of nonmelanoma type, the method comprising administering to a subject in need thereof an effective amount of the composition according to any of claims 2-4, 6-7.

10. A method of treating a subject in need of increasing melanin production in skin to protect against skin cancers of melanoma type, the method comprising administering to a subject in need thereof an effective amount of the composition according to any of claims 2-4, 6-7.

11. The method of claim 10 wherein the composition is formulated for topical application.

12. The method of claim 11 wherein the composition is formulated as a sunless tanning product having the one or more peptides in an amount effective to cause tanning on skin without ultraviolet radiation from sun.

13. A method of increasing melanin production of a subject, comprising administering to a subject in need thereof an effective amount of the composition according to any of claims 2-4, 6-7.

14. A method of increasing melanin production of a subject having a disorder involving pigment loss, comprising administration of a composition comprising an amount of one or more peptides effective to increase the melanin production, wherein the one or more peptides have an amino acid sequence at least 60% homologous to one of:

YSSWY, (SEQ ID NO: 1)
or
YRSRK, (SEQ ID NO: 2)

to a subject in need thereof, wherein the one or more peptides activates tyrosinase to increase melanin production in an epidermis of the subject, and wherein the composition is administered topically to the epidermis.

15. A method of increasing melanin production of a subject having vitiligo or other hypopigmentation disorders in the epidermis, comprising administration of a composition comprising an amount of one or more peptides effective to increase the melanin production, wherein the one or more peptides have an amino acid sequence at least 60% homologous to one of:

YSSWY, (SEQ ID NO: 1)
or
YRSRK, (SEQ ID NO: 2)

to a subject in need thereof, wherein the one or more peptides activate tyrosinase to increase melanin production in an epidermis of the subject.

16. A method of increasing melanin production of a subject having cancers of melanoma type or nonmelanoma type, comprising administration of a composition to a subject in need thereof comprising an amount of one or more peptides effective to increase the melanin production, wherein the one or more peptides have an amino acid sequence at least 60% homologous of:

```
                              (SEQ ID NO: 1)
YSSWY,
or
                              (SEQ ID NO: 2)
YRSRK,
``` wherein the one or more peptides activate tyrosinase to increase melanin production in an epidermis of the subject, and the epidermis has cancers of melanoma type or nonmelanoma type.

17. A method of increasing melanin production in epidermis of a subject, comprising administration to a subject in need thereof of a composition according to any of claims 2-4, 6-7.

* * * * *